(12) United States Patent
Press et al.

(10) Patent No.: US 8,084,463 B2
(45) Date of Patent: *Dec. 27, 2011

(54) QUINUCLIDINE DERIVATIVES AND THEIR USE AS MUSCARINIC M3 RECEPTOR ANTAGONISTS

(75) Inventors: Neil J Press, Horsham (GB); Stephen P Collingwood, Horsham (GB); Urs Baettig, Horsham (GB); Brian Cox, Horsham (GB); Sudhakar D Garad, Cambridge, MA (US); Hyungchul Kim, Cambridge, MA (US); Dimitris Papoutsakis, Cambridge, MA (US); Simon J Watson, Horsham (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,897

(22) Filed: Mar. 11, 2010

(65) Prior Publication Data

US 2010/0168132 A1 Jul. 1, 2010

Related U.S. Application Data

(63) Continuation of application No. 11/577,417, filed as application No. PCT/EP2005/011662 on Oct. 31, 2005, now Pat. No. 7,723,356.

(30) Foreign Application Priority Data

Nov. 2, 2004 (GB) .................................. 0424284.8

(51) Int. Cl.
*A61K 31/44* (2006.01)
(52) U.S. Cl. ........ 514/305; 544/322; 544/336; 546/133; 548/247; 549/74
(58) Field of Classification Search .................. 514/305; 544/322, 336; 546/133; 548/247; 549/74
See application file for complete search history.

(56) References Cited

U.S. PATENT DOCUMENTS 3,714,357 A 1/1973 Gueremy et al.

FOREIGN PATENT DOCUMENTS

| CL | 1703/1997 | 4/1998 |
|---|---|---|
| CL | 1889/2000 | 5/2001 |
| CL | 2031/2001 | 7/2002 |
| CL | 3158/2001 | 10/2002 |
| CL | 3193/2001 | 11/2002 |
| CL | 1246/2003 | 4/2004 |
| CL | 918/2004 | 2/2005 |
| CL | 528/2005 | 2/2006 |
| CL | 963/2005 | 4/2006 |
| CL | 1862/2005 | 7/2006 |
| EP | 1300407 | 4/2003 |
| FR | 2012964 | 3/1970 |
| WO | WO98/07722 | 2/1998 |
| WO | 01/04118 | 1/2001 |
| WO | WO02/15662 | 2/2002 |
| WO | WO02/16355 | 2/2002 |
| WO | WO02/16356 | 2/2002 |
| WO | WO02/16357 | 2/2002 |
| WO | WO02/16358 | 2/2002 |
| WO | WO02/17358 | 2/2002 |
| WO | WO02/535654 | 7/2002 |
| WO | WO2002/051841 | 7/2002 |
| WO | 03/053966 | 7/2003 |
| WO | WO2004/000840 | 12/2003 |
| WO | 2004/096800 | 11/2004 |
| WO | 2005/090342 | 9/2005 |
| WO | WO2005/104745 | 11/2005 |
| WO | WO2006/010452 | 2/2006 |

OTHER PUBLICATIONS

Jordon, V.C. Nature Reviews: Drug Discovery, 2, 2003, 205.
Berge, et al., J. Pharm. Sci., 66, (1), 1977, 1-19.
Serajuddin, A.T.M. Advanced Drug Delivery Reviews, 59, 2007, 603-616.
Dorwald, F. Zaragoza. Side Reactions in Organic Synthesis: A Guide to Successful Synthesis Design, Weinheim: WILEY-VCH Verlag GmbH & Co. KGaA, 2005, Preface.
Kumar, et al. Drug Discovery Today, 12, 23/24, 2007, 1048-1053.

*Primary Examiner* — James O Wilson
*Assistant Examiner* — Douglas M Willis
(74) *Attorney, Agent, or Firm* — Cozette M McAvoy

(57) ABSTRACT

Compounds of Formula (I); in salt or zwitterionic form wherein $R^1$, $R^2$, $R^3$ and $R^4$ have the meanings as indicated in the specification, are useful for treating conditions that are mediated by the muscarinic M3 receptor, especially inflammatory or obstructive airways diseases. Pharmaceutical compositions that contain the compounds and a process for preparing the compounds are also described.

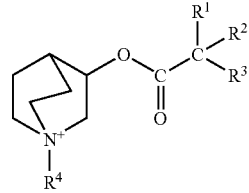

7 Claims, No Drawings

QUINUCLIDINE DERIVATIVES AND THEIR USE AS MUSCARINIC M3 RECEPTOR ANTAGONISTS

This application is a continuation of application Ser. No. 11/577,417, which is a National Stage of International Application No. PCT/EP2005/011662 filed on Oct. 31, 2005, which claims benefit of Great Britain Application No. 0424284.8 filed on Nov. 2, 2004, the entire disclosures of which are hereby incorporated by reference.

DETAILED DESCRIPTION OF THE INVENTION

This invention relates to organic compounds, their preparation and use as pharmaceuticals.

In one aspect the invention provides compounds of formula I

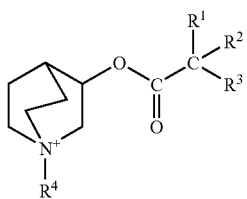

in salt or zwitterionic form wherein $R^1$ and $R^2$ are each independently phenyl, one or both of $R^1$ and $R^2$ being substituted at one, two or three positions by halo, $C_1$-$C_8$-alkyl or $C_1$-$C_8$-alkoxy, and $R^3$ is hydrogen, hydroxy, $C_1$-$C_8$-alkyl, $C_1$-$C_8$-alkoxy or $C_1$-$C_8$-alkylthio;

or $R^1$ and $R^2$ are each unsubstituted phenyl, and $R^3$ is hydrogen, $C_1$-$C_8$-alkyl, $C_1$-$C_8$-alkoxy or $C_1$-$C_8$-alkylthio;

or $R^1$ is $C_3$-$C_8$-cycloalkyl or a 4- to 6-membered heterocyclic group containing at least one ring heteroatom selected from nitrogen, oxygen and sulphur, $R^2$ is phenyl optionally substituted at one, two or three positions by halo, $C_1$-$C_8$-alkyl or $C_1$-$C_8$-alkoxy, or $R^2$ is a 4- to 6-membered heterocyclic group containing at least one ring heteroatom selected from nitrogen, oxygen and sulphur, and $R^3$ is hydrogen, hydroxy, $C_1$-$C_8$-alkoxy or $C_1$-$C_8$-alkylthio;

or —$CR^1R^2R^3$ denotes 9H-fluoren-9-yl, 9,10-dihydroanthracenyl-9-yl, 9-hydroxy-9,10-dihydroanthracenyl-9-yl, 9-hydroxy-9H-fluoren-9-yl, 9H-xanthen-9-yl, 9-hydroxy-9H-xanthen-9-yl, 5H-dibenzo[a,d]cyclohepten-5-yl or 5-hydroxy-5H-dibenzo[a,d]cyclohepten-5-yl;

and $R^4$ is $C_1$-$C_8$-alkyl substituted at one, two or three positions by —CO—N($R^5$)$R^6$ where $R^5$ is hydrogen or $C_1$-$C_8$-alkyl and $R^6$ is a 4- to 6-membered heterocyclic group containing at least one ring heteroatom selected from nitrogen, oxygen and sulphur;

or $R^1$ and $R^2$ are each unsubstituted phenyl, it is hydroxy, and $R^4$ is $C_1$-$C_8$-alkyl substituted at one, two or three positions by —CO—N($R^5$)$R^6$ where $R^5$ is hydrogen or $C_1$-$C_4$-alkyl and it is 5-methyl-3-isoxazolyl;

or $R^1$ and $R^2$ are each unsubstituted phenyl, $R^3$ is hydroxy, and $R^4$ is 1-ethyl substituted at one, two or three positions by —CO—N($R^5$)$R^6$ where $R^5$ is hydrogen or $C_1$-$C_4$-alkyl and $R^6$ is a 4- to 6-membered heterocyclic group containing at least one ring heteroatom selected from nitrogen, oxygen and sulphur;

with the proviso that the compound of formula I is not (R)-3-(2-Hydroxy-2,2-di-thiophen-2-yl-acetoxy)-1-(pyrazin-2-ylcarbamoyl-methyl)-1-azonia-bicyclo[2.2.2]octane, (R)-3-(2-Hydroxy-2,2-di-thiophen-2-yl-acetoxy)-1-(isoxazol-3-ylcarbamoylmethyl)-1-azonia-bicyclo[2.2.2]octane bromide or (R)-3-(2-Hydroxy-2,2-di-thiophen-2-yl-acetoxy)-1-(pyrimidin-4-ylcarbamoyl-methyl)-1-azoniabicyclo[2.2.2]octane bromide.

Terms used in the specification have the following meanings:

"Optionally substituted at one, two or three positions" means the group referred to can be substituted at one, two or three positions by any one or any combination of the radicals described.

"$C_1$-$C_8$-alkyl" as used herein denotes straight chain or branched alkyl having 1 to 8 carbon atoms. Preferably, $C_1$-$C_8$-alkyl is $C_1$-$C_4$-alkyl, especially methyl or ethyl.

"$C_3$-$C_8$-cycloalkyl" as used herein denotes cycloalkyl having 3 to 8 carbon atoms. Preferably "$C_3$-$C_8$-cycloalkyl" is "$C_3$-$C_8$-cycloalkyl", especially cyclopentyl or cyclohexyl.

"$C_1$-$C_8$-alkylthio" as used herein denotes $C_1$-$C_8$-alkyl as hereinbefore defined linked to —S—. Preferably "$C_1$-$C_8$-alkylthio" is "$C_1$-$C_4$-alkylthio".

"$C_1$-$C_8$-alkoxy" as used herein denotes straight chain or branched alkoxy having 1 to 8 carbon atoms Preferably, $C_1$-$C_8$-alkoxy is $C_1$-$C_4$-alkoxy, especially methoxy.

"Halo" or "halogen" as used herein denotes a element belonging to group 17 (formerly group VII) of the Periodic Table of Elements, which may be, for example, fluorine, chlorine, bromine or iodine. Preferably halo or halogen is fluoro, chloro or bromo.

"4- to 6-membered heterocyclic group containing at least one ring heteroatom selected from nitrogen, oxygen and sulphur" as used herein denotes a heterocyclic group, which may be saturated or unsaturated, that has 4 to 6 ring atoms. Suitable groups include azetidinyl, tetrahydrofuranyl, furyl/furanyl, pyrrolyl, pyrrolidinyl, pyrazolyl, imidazolyl, triazolyl, tetrazolyl, thienyl, thiazolyl, thiadiazolyl, isothiazolyl, oxadiazolyl, pyridinyl, oxazolyl, isoxazolyl, piperidinyl, pyridinyl, pyrazinyl, pyridazinyl, pyrimidinyl, piperazinyl, morpholinyl, triazinyl, oxazinyl, thiazolyl or tetrahydropyranyl. Preferred 4- to 6-membered heterocyclic groups include unsaturated groups such as furyl, pyrrolyl, thienyl/thiophenyl, thiazolyl, oxazolyl, isoxazolyl, pyridinyl, pyrazinyl, pyridazinyl, pyrimidinyl and triazinyl. The 4- to 6-membered heterocyclic group can be unsubstituted or substituted at one or more positions, e.g. 1, 2 or 3 positions, by any one or any combination of substituents. Preferred substituents include halo (e.g. fluoro, chloro or bromo), cyano, oxo, hydroxy, carboxy, nitro, phenyl, $C_1$-$C_8$-alkyl (e.g. methyl or ethyl), halo-$C_1$-$C_8$-alkyl (e.g. trifluoromethyl), $C_1$-$C_8$-alkylcarbonyl, di($C_1$-$C_8$-alkyl)sulfamoyl and $C_1$-$C_8$-alkoxy optionally substituted by aminocarbonyl. When $R^2$ is a to 6-membered heterocyclic group containing at least one ring heteroatom selected from nitrogen, oxygen and sulphur it is preferably a 5-membered heterocyclic group containing at least one ring heteroatom selected from oxygen and sulphur, for example furanyl and thiophenyl, especially 2-furanyl or 2-thiophenyl. When $R^6$ is a 4- to 6-membered heterocyclic group containing at least one ring heteroatom selected from nitrogen, oxygen and sulphur it is preferably a 5- or 6-membered heterocyclic group containing at least one ring heteroatom selected from oxygen and nitrogen, for example unsubstituted pyrazinyl, unsubstituted pyridazinyl or unsubstituted triazinyl, or oxazolyl optionally substituted at one, two or three positions by $C_1$-$C_4$-alkyl or phenyl, especially unsubstituted pyrazinyl, unsubstituted pyridazinyl, unsubstituted triazinyl, or oxazolyl optionally substituted at one position by methyl, ethyl or phenyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

Preferred compounds of formula I in salt or zwitterionic form include those where $R^1$ and $R^2$ are each independently phenyl, one or both of $R^1$ and $R^2$ being substituted by one halo, $C_1$-$C_4$-alkyl or $C_1$-$C_4$-alkoxy, and $R^3$ is hydroxy;

or $R^1$ and $R^2$ are each unsubstituted phenyl, and $R^3$ is hydrogen, $C_1$-$C_4$-alkyl, $C_1$-$C_4$-alkoxy or $C_1$-$C_4$-alkylthio;

or $R^1$ is $C_3$-$C_6$-cycloalkyl, $R^2$ is thiophenyl, furanyl or phenyl, and $R^3$ is hydroxy; or —$CR^1R^2R^3$ is 9-hydroxy-9H-fluoren-9-yl;

and $R^4$ is $C_1$-$C_4$-alkyl substituted at one, two or three positions by —CO—$NHR^6$ where $R^6$ is isoxazolyl optionally substituted by phenyl, or $R^6$ is pyrazinyl or pyrimidinyl;

or $R^1$ and $R^2$ are each unsubstituted phenyl, $R^3$ is hydroxy, and $R^4$ is $C_1$-$C_4$-alkyl substituted at one, two or three positions by —CO—$NHR^6$ where $R^6$ is 5-methyl-3-isoxazolyl;

or $R^1$ and $R^2$ are each unsubstituted phenyl, $R^3$ is hydroxy, and $R^4$ is 1-ethyl substituted at one, two or three positions by —CO—$NHR^6$ where $R^6$ is isoxazolyl.

Especially preferred compounds of formula I in salt or zwitterionic form include those where $R^1$ and $R^2$ are each independently phenyl, one or both of $R^1$ and $R^2$ being o-halophenyl, o- or p-$C_1$-$C_4$-alkylphenyl or o-, m- or p-$C_1$-$C_4$-alkoxyphenyl, and $R^3$ is hydroxy;

or $R^1$ and $R^2$ are each unsubstituted phenyl, and $R^3$ is hydrogen, $C_1$-$C_4$-alkyl, $C_1$-$C_4$-alkoxy or $C_1$-$C_4$-alkylthio;

or $R^1$ is $C_5$-$C_6$-cycloalkyl, $R^2$ is thiophenyl, furanyl or phenyl, and $R^3$ is hydroxy;

or —$CR^1R^2R^3$ is 9-hydroxy-9H-fluoren-9-yl;

and $R^4$ is methyl or 1-ethyl substituted at one position by —CO—$NHR^6$ where $R^6$ is isoxazol-3-yl optionally substituted at one position by phenyl, or $R^6$ is pyrazin-2-yl or pyrimidin-4-yl;

or $R^1$ and $R^2$ are each unsubstituted phenyl, $R^3$ is hydroxy, and $R^4$ is methyl substituted at one position by —CO—$NHR^6$ where $R^6$ is 5-methyl-isoxazol-3-yl;

or $R^1$ and $R^2$ are each unsubstituted phenyl, $R^3$ is hydroxy, and $R^4$ is 1-ethyl substituted at one position by —CO—$NHR^6$ where $R^6$ is isoxazol-3-yl.

The compounds of formula I are quaternary ammonium salts. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenylacetate, or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures. Compounds of formula I that contain acidic, e.g. carboxyl, groups may also exist as zwitterions with the quaternary ammonium centre.

The compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof. These isomers may be separated by conventional techniques, e.g. by fractional crystallization or column chromatography.

Specific especially preferred compounds of the invention are those described hereinafter in the Examples.

The invention also provides a process for the preparation of compounds of formula I which comprises (i) (A) reacting a compound of compound of formula II

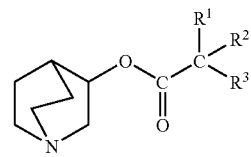

or a protected form thereof where $R^1$, $R^2$ and $R^3$ are as hereinbefore defined, with a compound of formula III

$R^4$—X where $R^4$ is as hereinbefore defined and X is chloro, bromo or iodo; or (B) reacting a compound of formula IV

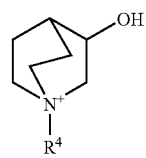

or a sodium salt thereof, where R⁴ is as hereinbefore defined, with a compound of formula V

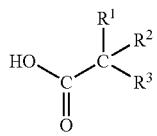

or an ester-forming derivative thereof, where R¹, R² and R³ are as hereinbefore defined; and (ii) recovering the product in salt or zwitterionic form.

Process variant (A) may be effected using known procedures for reacting quinuclidinol esters with halogenides or analogously as hereinafter described in the Examples. The reaction is conveniently carried out in water or an organic solvent, for example acetonitrile, dimethylformamide (DMF), dimethylsulphoxide (DMSO), ethyl acetate or chloroform. The reaction is carried out at a temperature between 20° C. to 120° C., conveniently between room temperature and 80° C.

Process variant (B) may be effected using known procedures for reacting hydroxy compounds or sodium salts thereof with carboxylic acids or ester-forming derivatives thereof such as acid halides or analogously as hereinafter described in the Examples. The reaction between an hydroxyl-substituted quinuclidine derivative and a carboxylic acid is conveniently carried out in an organic solvent, for example dimethylformamide (DAM, in the presence of a coupling agent, for example 1,1'-Carbonyldiimidazole (CDI), preferably in an inert atmosphere, for example under argon. Suitable reaction temperatures are from 0° C. to 60° C., preferably from 30° C. to 50° C., especially about 40° C.

Compounds of formula II are known or may be prepared by known procedures such as those disclosed in W. J. Rzeszotarski et al, *J. Med. Chem.* 1988, 31, 1463, international patent publication WO 01/04118 and U.S. Pat. No. 3,833,592, or analogously as hereinafter described in the Examples.

Compounds of formula III, IV or V are known or may be prepared by known procedures or analogously as hereinafter described in the Examples.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula I are quaternary ammonium salts and may be converted between different salt forms using ion exchange chromatography. The compounds can be obtained in the form of hydrates or solvates containing a solvent used for crystallization. Compounds of formula I can be recovered from reaction mixtures and purified using known methods. Isomers, such as enantiomers, may be obtained in a conventional manner, e.g. by fractional crystallization, chiral phase chromatography or asymmetric synthesis from correspondingly asymmetrically substituted, e.g. optically active, starting materials.

Compounds of formula I in pharmaceutically acceptable salt or zwitterionic form, hereinafter referred to alternatively as agents of the invention, are useful as pharmaceuticals. Accordingly the invention also provides a compound of formula I in pharmaceutically acceptable salt or zwitterionic form for use as a pharmaceutical. The agents of the invention act as muscarinic antagonists, particularly muscarinic M3 receptor antagonists, thereby inhibiting acetylcholine-induced contraction of smooth muscle in e.g. respiratory tract, digestive tract and urinary systems.

The affinity (Ki) of agents of the invention at the human muscarinic acetylcholine M3 receptor can be determined in a competitive filtration binding assay with the radio-labelled antagonist [³H] n-methyl scopolamine methyl chloride (NMS):

Membranes prepared from CHO cells stably transfected with human M3 receptor at 10 μg protein/well are incubated with serial dilutions of the agents of the invention, [³H]NMS (0.25 nM) and assay buffer (20 mM HEPES, 1 mM MgCl₂ at pH 7.4) for 17 hours at room temperature. The assay is carried out in a 250 μL final volume, in the presence of a final dimethyl sulfoxide concentration of 1%. Total binding of [³H]NMS is determined in the absence of the agents of the invention with a corresponding substituted volume of assay buffer. Non-specific binding of [³H] NMS is determined in the presence of 300 nM ipratropium bromide. Following the incubation period, the membranes are harvested onto a Unifilter™ GF/B filter plate containing 0.05% polyethyleneimine, using a Brandel™ filtration harvester 9600. Filter plates are dried for two hours at 35° C. before the addition of Microscint™ 'O' cocktail, and read on a Packard Topcount™ scintillator using a ³H-Scintillation protocol. All IC50s are calculated with the aid of XL-Fit graph package and $K_i$ values derived using the Cheng-Prusoff correction (Cheng Y., Prusoff W. H. (1973) Biochem. Pharmacol 22 3099-3109).

The compounds of the Examples herein below generally have Ki values below 1 μM in the above assay. For instance, the compounds of Examples 1, 2, 4, 5 and 8 have M3 $K_i$ values of 2.3, 1.4, 0.65, 0.63 and 0.75 nM respectively. The compounds of Examples 8, 10 and 11 have M3 pKi values of 10.9, 10.94 and 11.2 respectively.

Having regard to their inhibition of acetyl choline binding to M3 muscarinic receptors, agents of the invention are useful in the treatment of conditions mediated by the muscarinic M3 receptor, particularly those associated with increased parasympathetic tone leading to, for example, excessive glandular secretion or smooth muscle contraction. Treatment in accordance with the invention may be symptomatic or prophylactic.

Having regard to their antimuscarinic activity, the agents of the invention are useful in the relaxation of bronchial smooth muscle and the relief of bronchoconstriction. Relief of bronchoconstriction can be measured in models such as the in vivo plethysmography models of Chong et al, *J. Pharmacol. Toxicol. Methods* 1998, 39, 163, Hammelmann et al, *Am. J. Respir. Crit. Care Med.,* 1997, 156, 766 and analogous models. The agents of the invention are therefore useful in the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with β₂ agonists such as tachycardia, tremor and restlessness, such agents accordingly being suitable for use in on demand (rescue) treatment as well as prophylactic treatment of obstructive or inflammatory airways diseases.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their antimuscarinic activity, the agents of the invention are also useful in the treatment of a condition requiring relaxation of smooth muscle of the uterus, bladder or vascular system. They are thus useful for the prevention or alleviation of premature labour pains in pregnancy. They are also useful in the treatment of chronic and acute urticaria, psoriasis, allergic conjunctivitis, actinitis, rhinitis including allergic rhinitis, mastocytosis, urinary disorders such as urinary incontinence (particularly that caused by overactive bladder), pollakiuria, neurogenic or unstable bladder, cytospasm and chronic cystitis; gastrointestinal disorders such as irritable bowel syndrome, spastic colitis, diverticulitis and peptic ulceration; and cardiovascular disorders such as vagally induced sinus bradycardia, as well as in ophthalmic interventions.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s). Accordingly the invention includes a combination of an agent of the invention as hereinbefore described with an anti-inflammatory, bronchodilatory, antihistamine, decongestant or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

The agents of the invention are useful in combination therapy with chemokine receptor antagonists, calcium channel blockers, alpha-adrenoceptor antagonists, dopamine agonists, endothelin antagonists, substance-P antagonists, 5-LO inhibitors, VLA-4 antagonists and theophylline.

The agents of the invention are also particularly useful as co-therapeutic agents for use in combination with beta-2 adrenoceptor agonists. Suitable beta-2 adrenoceptor agonists include albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 0075114, which document is incorporated herein by reference, preferably compounds of the Examples thereof, especially a compound of formula

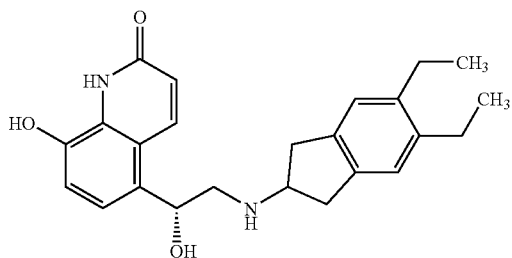

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, US 2005/0133417, US 2005/5159448, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103, WO 05/044787, WO 05/058867, WO 05/065650, WO 05/066140 and WO 05/07908.

Co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and one or more of beta-2 adrenoceptor agonists, steroids, PDE4 inhibitors, A2a agonists, A2b agonists and LTD4 antagonists may be used, for example, in the treatment of asthma but particularly COPD.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising a compound of formula I in free form or in the form of a pharmaceutically acceptable salt or solvate thereof, optionally together with a pharmaceutically acceptable diluent or carrier thereof. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture, such as magnesium stearate, e.g. 0.01 to 1.5%. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

Especially preferred compounds of formula I include compounds of formula VI

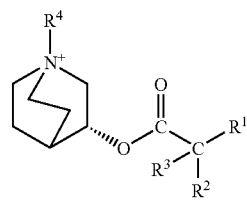

VI where $R^1$, $R^2$, $R^3$ and $R^4$ are as shown in Table 1 below, the method of preparation being described hereinafter. All compounds are quaternary ammonium salts. The table also shows mass spectrometry data. The compounds of Examples 8-11, 15-17 and 19-28 are a mixtures of diastereomers at hydroxyl-position. The compounds of Examples 29, 30 and 31 are phosphate salts of single enantiomers. In the table 10, $R^2$ and $R^3$ together with the carbon atom to which they are attached are represented as a moiety having the formula —$CR^1R^2R^3$.

TABLE 1
| Ex. | R¹ | R² | R³ | R⁴ | M/s M+ |
|---|---|---|---|---|---|
| 1 | 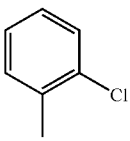 | 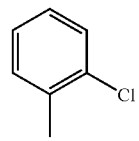 | —OH | 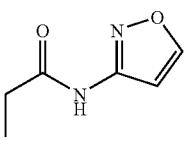 | 530.3 |
| 2 | 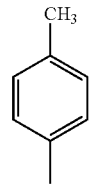 | 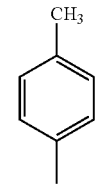 | —OH | 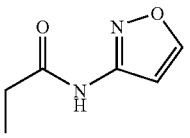 | 490.3 |
| 3 | 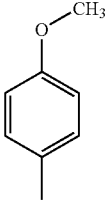 | 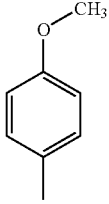 | —OH | 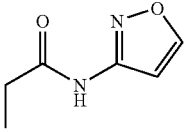 | 522.3 |
| 4 | 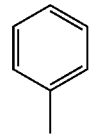 | 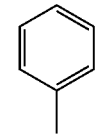 | —CH₃ | 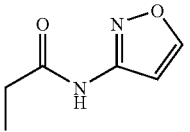 | 427.5 |
| 5 | 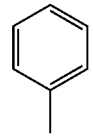 | 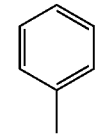 | —H | 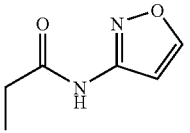 | 446.4 |
| 6 | 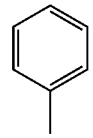 | 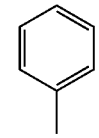 | —OCH₃ | 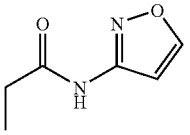 | 476.3 |
| 7 | 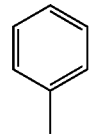 | 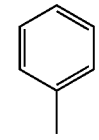 | —SCH₂CH₃ | 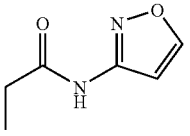 | 506.3 |
| 8 | 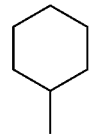 | 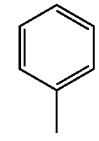 | —OH | 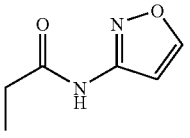 | 468.2 |
| 9 |  | 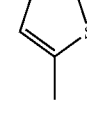 | —OH | 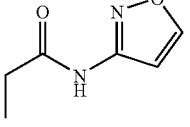 | 460.2 |

TABLE 1-continued

| Ex. | R¹ | R² | R³ | R⁴ | M/s M+ |
|---|---|---|---|---|---|
| 10 | cyclohexyl-CH₂– | 2-thienyl-CH₂– | —OH | –CH₂CH₂C(O)NH-isoxazol-3-yl | 474.2 |
| 11 | cyclopentyl-CH₂– | phenyl-CH₂– | —OH | –CH₂CH₂C(O)NH-isoxazol-3-yl | 454.4 |
| 12 | 9-hydroxy-9-methyl-fluorenyl | | | –CH₂CH₂C(O)NH-isoxazol-3-yl | 460.4 |
| 13 | phenyl-CH₂– | phenyl-CH₂– | —OH | –CH₂CH₂C(O)NH-(5-methylisoxazol-3-yl) | 476.4 |
| 14 | phenyl-CH₂– | phenyl-CH₂– | —OH | –CH(CH₃)C(O)NH-isoxazol-3-yl | 476.6 |
| 15 | cyclopentyl-CH₂– | phenyl-CH₂– | —OH | –CH₂CH₂C(O)NH-pyrazin-2-yl | 465.4 |
| 16 | cyclohexyl-CH₂– | phenyl-CH₂– | —OH | –CH₂CH₂C(O)NH-pyrimidin-4-yl | 479.5 |
| 17 | cyclohexyl-CH₂– | phenyl-CH₂– | —OH | –CH₂CH₂C(O)NH-(4-phenylisoxazol-3-yl) | 544.4 |
| 18 | 3-methoxyphenyl-CH₂– | 3-methoxyphenyl-CH₂– | —OH | –CH₂CH₂C(O)NH-isoxazol-3-yl | 522.4 |

TABLE 1-continued

| Ex. | R¹ | R² | R³ | R⁴ | M/s M+ |
|---|---|---|---|---|---|
| 19 | cyclopentylmethyl | 2-thienylmethyl | —OH | propanoylamino-pyrazine | 471.4 |
| 20 | cyclohexylmethyl | benzyl | —OH | propanoylamino-pyrazine | 479.5 |
| 21 | cyclopentylmethyl | benzyl | —OH | propanoylamino-pyrazine | 465.2 |
| 22 | 4-methoxybenzyl | benzyl | —OH | propanoylamino-isoxazole | 492.3 |
| 23 | 2-methylbenzyl | benzyl | —OH | propanoylamino-isoxazole | 476.3 |
| 24 | 2-methoxybenzyl | benzyl | —OH | propanoylamino-isoxazole | 492.3 |
| 25 | cyclopentylmethyl | benzyl | —OH | propanoylamino-pyrimidine | 465.5 |
| 26 | cyclopentylmethyl | 2-thienylmethyl | —OH | propanoylamino-pyrimidine | 471.4 |
| 27 | cyclohexylmethyl | 2-thienylmethyl | —OH | propanoylamino-pyrimidine | 485.5 |

TABLE 1-continued

| Ex. | R¹ | R² | R³ | R⁴ | M/s M+ |
|---|---|---|---|---|---|
| 28 | cyclopentyl | 2-furyl | —OH | NH-isoxazol-3-yl) | 444.4 |
| 29 | cyclohexyl | 2-thienyl | —OH | C(=O)NH-isoxazol-3-yl | 474 |
| 30 | cyclohexyl | phenyl | —OH | C(=O)NH-isoxazol-3-yl | 468.3 |
| 31 | cyclopentyl | phenyl | —OH | C(=O)NH-isoxazol-3-yl | 454 |

Preparation of Intermediate Compounds

Abbreviations used are as follows: CDI is 1,1'-Carbonyldiimidazole, DCM is dichloromethane, DMF is dimethylformamide, HPLC is High Performance Liquid Chromatography, LC-MS is Liquid Chromatography Mass Spectrometry, and THF is tetrahydrofuran.

Intermediate A (R)-3-Hydroxy-1-(isoxazol-3-ylcarbamoylmethyl)-1-azonia-bicyclo[2.2.2]octane bromide Ai) 2-Bromo-N-isoxazol-3-yl-acetamide To a stirred solution of bromoacetylbromide (5.36 ml, 61.6 mmol) in diethylether (100 ml) at −40° C. is added, dropwise over 20 minutes, a solution of 3-aminoisoxazol (5.0 ml, 67.0 mmol) and triethylamine (8.5 ml, 61.4 mmol) in diethylether (20 ml). Additional diethylether (50 ml) is added and stirring continued for 3 hours. The reaction mixture is filtered and the solution then washed with 1 M sodium carbonate solution, 1 M hydrochloric acid and brine. Concentration followed by purification by flash silica column chromatography (ethyl acetate/iso-hexane 4:7) gives the title compound as a white solid.

Aii) (R)-3-Hydroxy-1-(isoxazol-3-ylcarbamoylmethyl)-1-azonia-bicyclo[2.2.2]octane bromide A solution comprising 2-bromo-N-isoxazol-3-yl-acetamide (0.975 g, 4.72 mmol), (R)-1-aza-bicyclo[2.2.2]octan-3-ol (0.549 g, 4.32 mmol) in chloroform/acetonitrile (1:1) (10 ml) is stirred at room temperature for 30 minutes. The resultant precipitate is filtered, washed with chloroform/acetonitrile (1:1) and dried under vacuum to yield the titled compound as a white solid.

Intermediate B

Hydroxy-di-p-tolyl-acetic acid

A mixture of potassium hydroxide (1.7 g, 30.4 mmol) and n-butanol (9 ml) is heated to 120° C. until a solution forms. To this solution is added 4,4'-dimethylbenzil (3.1 g, 13.0 mmol) in one portion. Heating continues for a further 10 minutes and then, the reaction mixture is allowed to cool to room temperature. The reaction mixture is partitioned between water (40 ml) and diethyl ether (30 ml) and the aqueous layer is isolated and acidified to pH4. The aqueous is extracted with diethyl ether (50 ml) and the organic portions are combined, washed with brine, dried over MgSO₄ and concentrated in vacuo. The resulting oil is triturated with hexane and toluene to yield the titled compound.

Intermediate C

Hydroxy-bis-(4-methoxy-phenyl)-acetic acid

This compound is prepared by an analogous method to hydroxy-di-p-tolyl-acetic acid (Intermediate B) by replacing 4,4'-dimethylbenzil with 4,4'-dimethoxybenzil.

Intermediate D

Cyclopentyl-H-hydroxy-thiophen-2-yl-acetic acid

To a stirred suspension of magnesium (0.232 g, 9.7 mmol) in ether (5 ml) under an atmosphere of argon is added iodine (catalytic amount). After 5 minutes, the reaction mixture is treated with cyclopentyl bromide (2 ml, 9.7 mmol) in ether (5 ml) portionwise over 10 minutes and is then stirred at room temperature for 20 minutes. Meanwhile, a second reaction vessel comprising 2-thiopheneglyoxcylic acid (1 g, 6.5 mmol) in ether (10 ml) cooled to 0° C. is treated with sodium hydride (0.26 g of a 60% dispersion in mineral oil, 6.5 mmol). The reaction mixture is stirred for 30 minutes and then the grignard reagent (prepared as described above) is added portion wise over 5 minutes. After stirring at room temperature for 4 hours, the reaction mixture is partitioned between water (100 ml) and ethyl acetate (100 ml). The aqueous layer is acidified to pH 1 with 1M hydrochloric acid and then extracted with ethyl acetate (50 ml). The organic portions are combined, washed with brine, dried over magnesium sulphate and evaporated in vacuo, to yield the titled compound as a yellow solid.

Intermediate E

Cyclohexyl-hydroxy-thiophen-2-yl-acetic acid

This compound is prepared by an analogous method to cyclopentyl-H-hydroxy-thiophen-2-yl-acetic acid (Intermediate D) by replacing cyclopentyl magnesium bromide with cyclohexyl magnesium bromide.

Intermediate F (R)-3-Hydroxy-1-[(5-methyl-isoxaol-3-ylcarbamoyl)-methyl]-1-azonia-bicyclo[2.2.2]octane bromide Fi) 2-Bromo-N-(5-methyl-isoxazol-3-yl)-acetamide To a stirred solution of S-methyl-isoxazol-3-ylamine (4.0 g, 40.8 mmol) and triethylamine (6.8 ml, 50 mmol) in chloroform (20 ml) cooled to −40° C., is added bromoacetyl bromide (3.9 ml, 44.9 mmol) in chloroform (20 ml). The reaction mixture is stirred at −40° C. for 30 minutes and then allowed to warm to room temperature. The resultant suspension is filtered, washed with DCM and dried in vacuo to yield the titled compound.

Fii) (R)-3-Hydroxy-1-[(5-methyl-isoxazol-3-ylcarbamoyl)-methyl]-1-azonia-bicyclo[2.2.2]octane bromide This compound is prepared analogously to (R)-3-hydroxy-1-(isoxazol-3-ylcarbamoylmethyl)-1-azonia-bicyclo[2.2.2]octane bromide [Intermediate A] by substituting 2-bromo-N-isoxazol-3-yl-acetamide (in step Aii) with 2-bromo-N-(5-methyl-isoxazol-3-yl)-acetamide.

Intermediate G (R)-3-Hydroxy-1-[1-(isoxazol-3-ylcarbamoyl)-ethyl]-1-azonia-bicyclo[2.2.2]octane bromide Gi) 2-Bromo-N-isoxazol-3-yl-propionamide To a cooled (−40° C.) stirring solution of 3-aminoisoxazole (0.88 ml, 11.9 mmol) and triethylamine (1.99 ml, 14.3 mmol) in chloroform (6 ml) is added slowly, 2-bromopropionyl bromide (1.37 ml, 13.1 mmol) in chloroform (6 ml). The reaction mixture is stirred at −40° C. for 30 minutes, and then allowed to warm to room temperature. The mixture is then partitioned between 1M aqueous hydrochloric acid and ethyl acetate. The organic extract is washed with saturated sodium hydrogen carbonate, dried over $Na_2SO_4$ and the solvent removed in vacuo to afford the titled compound as a yellow oil.

Gii) (R)-3-Hydroxy-1-[1-(isoxazol-3-ylcarbamoyl)-ethyl]-1-azonia-bicyclo[2.2.2]octane bromide To a stirred solution of (R)-1-aza-bicyclo[2.2.2]octan-3-ol (0.267 g, 2.1 mmol) in chloroform/acetonitrile (1:1) (4 ml) is added 2-bromo-N-isoxazol-3-yl-propionamide [G(i)](0.5 g, 2.28 mmol) and the reaction mixture heated in a microwave at 90° C. for 3 hours. Purification using C-18 reverse phase column chromatography (eluent: water-acetonitrile) yields the titled compound.

Intermediate H (R)-3-Hydroxy-1-(pyrazin-2-ylcarbamoylmethyl)-1-azonia-bicyclo[2.2.2]octane bromide Hi) 2-Bromo-N-pyrazin-2-yl-acetamide To a cooled (0° C.) solution of 2-aminopyrazine (4.98 g, 52 mmol) in dichloromethane (50 ml) and dimethylformamide (20 ml) is added dropwise a solution of bromoacetic anhydride (15 g, 57 mmol) in dichloromethane. The reaction mixture is stirred for 3 hours at 0° C. and then purification by flash column chromatography on silica (eluent: 1% ammonia solution/5% methanol/94% dichloromethane) affords the titled compound as a light brown solid.

Hii) (R)-3-Hydroxy-1-(pyrazin-2-ylcarbamoylmethyl)-1-azonia-bicyclo[2.2.2]octane bromide This compound is prepared by an analogous method to (R)-3-hydroxy-1-(isoxazol-3-ylcarbamoylmethyl)-1-azonia-bicyclo[2.2.2]octane bromide (Intermediate A) by replacing 2-bromo-N-isoxazol-3-yl-acetamide with 2-bromo-N-pyrazin-2-yl-acetamide [H(i)].

Intermediate I (R)-3-Hydroxy-1-[(4-phenyl-isoxazol-3-ylcarbamoyl)-methyl]-1-azonia-bicyclo[2.2.2]octane bromide This compound is prepared by an analogous method to (R)-3-hydroxy-1-(isoxazol-3-ylcarbamoylmethyl)-1-azonia-bicyclo[2.2.2]octane bromide (Intermediate A) by replacing in 3-aminoisoxazol in step (Ai) with 4-phenylisoxazol-3-ylamine.

Intermediate J

Hydroxy-bis-(3-methoxy-phenyl)-acetic acid

This compound is prepared by an analogous method to hydroxy-di-p-tolyl-acetic acid (Intermediate B) by replacing 4,4'-dimethylbenzil with 3,3'-dimethoxy benzyl.

Intermediate K

Hydroxy-bis-(3-methoxy-phenyl)-acetic acid (R)-(1-aza-bicyclo[2.2.2]oct-3-yl)ester To a stirred solution of hydroxy-bis-(3-methoxy-phenyl)-acetic acid (Intermediate J) (1.384 g, 4.8 mmol) in dry THF (2.0 ml) is added CDI (0.870 g, 5.3 mmol) and the mixture is heated to reflux for 90 minutes. (R)-1-aza-bicyclo[2.2.2]octan-3-ol (0.67 g, 5.3 mmol) is then added. After refluxing for 16 hours, the reaction mixture is diluted with ethyl acetate and washed with water. The organic layer is then extracted with 2M HCl and the aqueous portion is treated with potassium carbonate to basify the solution. The aqueous portion is re-extracted with ethyl acetate. The organic portions are combined, dried over $MgSO_4$ and concentrated in vacuo to yield a crude residue which is purified using C-18 reverse phase column chromatography (eluent: water-acetonitrile), to afford the titled compound.

Intermediate L

Hydroxy-(4-methoxy-phenyl)-phenyl-acetic acid

This compound is prepared by an analogous method to hydroxy-di-p-tolyl-acetic acid (Intermediate B) by replacing 4,4'-dimethylbenzil with 4-methoxy benzyl.

Intermediate M

Hydroxy-phenyl-o-tolyl-acetic acid

To a stirred suspension of magnesium (0.773 g, 31.81 mmol), iodine (cat. Amount) in THF (20 ml) is added dropwise, bromotoluene (3.83 ml, 31.81 mmol) in THF (30 ml). The reaction mixture is warmed to initiate the reaction and then allowed to stir at room temperature for 30 minutes. Meanwhile, a second mixture comprising benzoyl formic acid (4.342 g, 28.92 mmol) in THF (50 ml) is cooled in an ice bath. Sodium hydride (1.156 g of a 60% dispersion in mineral oil, 28.92 mmol) is added to the mixture, portionwise, ensuring the temperature does not rise above 10° C. Then the grignard reagent which has been stirring for 30 minutes is added dropwise and the reaction mixture is allowed to warm to room temperature. After stirring for 21 hours, the reaction mixture is partitioned between ethyl acetate (150 ml) and water (150 ml). The aqueous layer is acidified to pH 1 with 1 M hydrochloric acid and then extracted with ethyl acetate. The organic portions are combined, washed with brine, dried over $MgSO_4$ and concentrated in vacuo. The crude residue is purified by chromatography on silica (eluting with ethyl acetate) to yield the titled compound.

Intermediate N

Hydroxy-(2-methoxy-phenyl)-phenyl-acetic acid

This compound is prepared by an analogous method to hydroxy-phenyl-o-tolyl-acetic acid (Intermediate M) by replacing bromotoluene with 2-bromomethoxy benzene and benzoyl formic acid with methyl benzoyl formate.

Intermediate O

Hydroxy-(4-methoxy-phenyl)-phenyl-acetic acid (R)-(1-aza-bicyclo[2.2.2]oct-3-yl)ester This compound is prepared by an analogous method to hydroxy-bis-(3-methoxy-phenyl)-acetic acid (R)-(1-aza-bicyclo[2.2.2]oct-3-yl)ester (Intermediate K) by replacing hydroxy-bis-(3-methoxy-phenyl)-acetic acid (Intermediate J) with hydroxy-(4-methoxy-phenyl)-phenyl-acetic acid (Intermediate L).

Intermediate P

Hydroxy-phenyl-o-tolyl-acetic acid (R)-(1-aza-bicyclo[2.2.2]oct-3-yl)ester

This compound is prepared by an analogous method to hydroxy-bis-(3-methoxy-phenyl)-acetic acid (R)-(1-aza-bicyclo[2.2.2]oct-3-yl)ester (Intermediate K) by replacing hydroxy-bis-(3-methoxy-phenyl)-acetic acid (Intermediate J) with hydroxy-phenyl-o-tolyl-acetic acid (Intermediate M).

Intermediate Q (R)-3-Hydroxy-1-(pyrimidin-4-ylcarbamoylmethyl)-1-azonia-bicyclo[2.2.2]octane bromide Qi) 2-Bromo-N-pyrimidin-4-yl-acetamide To a stirred solution of 4-amino pyridine (12.0 g, 126 mmol) in DCM (192 ml) under an atmosphere of nitrogen is added triethylamine (23.1 ml, 164 mmol) and the resultant suspension is cooled to 0-5° C. To the cooled solution is added dropwise bromoacetic anhydride (42.6 g, 164 mmol) is DCM (48 ml) maintaining the temperature below 5° C. The resulting solid is filtered, washed with DCM and dried in vacuo to yield the titled compound.

Qii) (R)-3-Hydroxy-1-(pyrimidin-4-ylcarbamoylmethyl)-1-azonia-bicyclo[2.2.2]octane bromide This compound was prepared by an analogous method to (R)-3-Hydroxy-1-(isoxazol-3-ylcarbamoylmethyl)-1-azonia-bicyclo[2.2.2]octane bromide (Intermediate A) by replacing 2-bromo-N-isoxazol-3-yl-acetamide (Ai) with 2-bromo-N-pyrimidin-4-yl-acetamide (Qi).

Intermediate R (S)-Cyclohexyl-hydroxy-thiophen-2-yl-acetic acid (R)-(1-aza-bicyclo[2.2.2]oct-3-yl)ester Ri) Cyclohexyl-hydroxy-thiophen-2-yl-acetic acid ethyl ester To a stirred, cooled (0° C.) solution of ethyl thiophene-2-glyoxylate (125.6 g, 0.683 mol) in diethyl ether (2 litres) is added dropwise 2M cyclohexyl magnesium chloride in ether (400 ml, 0.8 mol) over 1 hour. After stirring at room temperature for 2 hours, the reaction is quenched by addition of saturated ammonium chloride solution (1 litre of a 270 g/l solution) and water (1 litre) ensuring the temperature does not rise above 20° C. The organic portion is separated and washed with brine (1 litre), dried over magnesium sulphate and concentrated in vacuo, to yield the titled compound as an orange oil which is used in the next step without further purification.

Rii) Cyclohexyl-hydroxy-thiophen-2-yl-acetic acid

A solution of cyclohexyl-hydroxy-thiophen-2-yl-acetic acid ethyl ester (361.8 g, 1.35 mol) in MeOH (1.5 litres) and THF (1.5 litres) is treated portionwise with 2M NaOH (1.1 litres) over 30 minutes. The reaction mixture is stirred at room temperature overnight and then concentrated in vacuo to remove the organic solvents. The remaining aqueous portion is partitioned between EtOAc (2 litres) and 20% citric acid in water (1 litre). The organic layer is separated, washed with brine and concentrated in vacuo to afford the titled compound which is used crude in the next step.

Riii) (S)-Cyclohexyl-hydroxy-thiophen-2-yl-acetic acid

L-cinchonidine (30.2 g, 0.103 mol) is added to crude cyclohexyl-hydroxy-thiophen-2-yl-acetic acid (49.3 g, 103 mol assuming 50% purity of crude) followed by toluene (2.2 litres) and the mixture is heated to reflux for 70 minutes. The resulting solution is allowed to cool slowly and at 65° C., the solution is seeded. After further cooling to 40° C., the solution is placed in the fridge overnight. The resulting solid is filtered, washed with toluene and dried in vacuo. The recrystallisation process from toluene is repeated for a second time with seeding occurring at 85° C. to afford the titled compound as a salt of L-cinchonidine in 98% enantiomeric excess. The salt is added to a stirred mixture of 1M HCl (40 ml) and diethyl ether (500 ml) and stirring continues until a solution forms. The organic portion is separated, washed with brine (400 ml), dried over MgSO$_4$ and concentrated in vacuo to give the titled compound in 98% enantiomeric excess.

Riv) (S)-Cyclohexyl-hydroxy-thiophen-2-yl-acetic acid (R)-(1-aza-bicyclo[2.2.2]oct-3-yl)ester To a stirred, cooled (10° C.) suspension comprising sodium hydride (24.6 g, of a 60% dispersion in oil, 0.614 mol) in DMF (450 ml) is added portionwise R-3-quinuclidinol (52.1 g, 0.409 mol) over 40 minutes and the resulting mixture is allowed to stir at 10° C. for 90 minutes. In the meantime, a second reaction vessel comprising (S)-cyclohexyl-hydroxy-thiophen-2-yl-acetic acid (98.4 g, 0.409 mol) in DMF (450 ml) is cooled to 10° C. and treated portionwise with CDI (73.0 g, 0.45 mol) over 30 minutes. After stirring at 10° C. for 90 minutes, this mixture is added dropwise to the cooled (10° C.) suspension of the sodium salt of R-3-quinucliodinol. After stirring at 10° C. for 1 hour, water (1 litre) is added dropwise over 30 minutes ensuring the temperature remains below 15° C. The resulting slurry is stirred at 10° C. for 30 minutes and then filtered, washed with water (2×150 ml) and then dried in vacuo over phosphorus pentoxide to afford the titled compound.

Intermediate S

(R)-Cyclohexyl-hydroxy-phenyl-acetic acid (R)-(1-aza-bicyclo[2.2.2]oct-3-yl)ester

Si) (R)-2-tert-Butyl-5-phenyl-[1,3]dioxolan-4-one

To a suspension comprising R-(−)mandelic acid (160 g, 1.05 mol) in pentane (1.5 litres) is added trimethyl acetaldehyde (145 ml, 1.31 mol) followed by triflic acid (3.96 ml, 0.04 mol). The resulting mixture is heated to reflux and stirred overnight. The solvent is removed in vacuo and the crude material is dissolved in ethyl acetate (3.1 litres). This organic portion is washed with saturated sodium bicarbonate solution (2.4 litres), water (2.4 litres), brine (2.4 litres), dried over MgSO$_4$ and concentrated in vacuo at 40° C. to afford the titled product.

Sii) (2R,5S)-2-tert-Butyl-5-(1-hydroxy-cyclohexyl)-5-phenyl-[1,3]dioxolan-4-one To a cooled (−78° C.) solution of 1 M lithium bis(trimethylsilyl)amide in hexanes (1 litre, 1 mol) is added dropwise (R)-2-tert-butyl-5-phenyl-[1,3]dioxolan-4-one (170 g, 0.77 mol) in THF (1.1 litre) over 90 minutes ensuring the temperature does not exceed −70° C. After stirring at −78° C. for 1 hour, cyclohexanone (112 ml, 1.1 mol) is added dropwise over 15 minutes and then stirring continued at −78° C. for another hour. The reaction is quenched by addition of 10% aqueous ammonium chloride solution (170 ml) and after warming to −20° C., a further 2 litres of 10% aqueous ammonium chloride solution is added. The aqueous portion is separated and extracted with EtOAc (500 ml). The organic portions are combined, dried over MgSO$_4$ and concentrated in vacuo. The resulting crude product is slurried in heptane for 20 minutes and then filtered and dried in vacuo to afford the titled compound as a white solid.

Siii) (S)-Cyclohex-1-enyl-hydroxy-phenyl-acetic acid (2R,5S)-2-tert-Butyl-5-(1-hydroxy-cyclohexyl)-5-phenyl-[1,3]dioxolan-4-one (176 g, 0.553 mol) in THF (1.56 litres) is cooled to 0° C. and treated dropwise with thionyl chloride (109 ml, 1.49 mol) followed by pyridine (191 ml, 2.35 mol) over 40 minutes. After stirring at 0° C. for 30 minutes, the reaction is quenched by dropwise addition of saturated ammonium chloride solution (2000 ml) ensuring the temperature does not exceed 25° C. Water (300 ml) is added and the organic portion is separated. The aqueous is extracted with EtOAc (1000 ml) and the combined organic layers are washed with brine and concentrated in vacuo. To the resulting crude material is added MeOH (333 ml) followed by water (586 ml). The mixture is stirred and treated with potassium hydroxide (221.2 g, 5.53 mol) maintaining the temperature below 50° C. The reaction mixture is heated to reflux for 3.5 hour and then allowed to cool to room temperature. The methanol is removed in vacuo and the aqueous is cooled to 0° C. The solution is acidified to pH1 with 5M HCl and then diluted with water (1 litre). The solution is extracted with EtOAc (2×1 litre) and the combined organic portions are dried (Na$_2$SO$_4$) and concentrated in vacuo to afford the titled product.

Siv) (R)-Cyclohexyl-hydroxy-phenyl-acetic acid (S)-cyclohex-1-enyl-hydroxy-phenyl-acetic acid (120 g, 0.517 mol) is dissolved in methanol (678 ml) under an inert atmosphere of Argon and then treated with palladium on carbon (6 g, 10% w/w). The resulting suspension is stirred under an atmosphere of hydrogen for 22 hours and then filtered through celite. The solvent is removed in vacuo to yield the titled product.

Sv) (R)-Cyclohexyl-hydroxy-phenyl-acetic acid (R)-(1-aza-bicyclo[2.2.2]oct-3-yl)ester This compound is prepared analogously to (S)-cyclohexyl-hydroxy-thiophen-2-yl-acetic acid (R)-(1-aza-bicyclo[2.2.2]oct-3-yl)ester by replacing (S)-cyclohexyl-hydroxy-thiophen-2-yl-acetic acid with (R)-cyclohexyl-hydroxy-phenyl-acetic acid.

Intermediate T

(R)-Cyclopentyl-hydroxy-phenyl-acetic acid

Ti) (2R,5S)-2-tert-Butyl-5-(1-hydroxy-cyclopentyl)-5-phenyl-[1,3]dioxolan-4-one This compound is prepared analogously to (2R,5S)-2-tert-butyl-5-(1-hydroxy-cyclohexyl)-5-phenyl-[1,3]dioxolan-4-one by replacing cyclohexanone with cyclopentanone.

Tii) (R)-Cyclopentyl-hydroxy-phenyl-acetic acid

This compound is prepared analogously to (R)-cyclohexyl-hydroxy-phenyl-acetic acid (Intermediate Siv) by replacing (2R,5S)-2-tert-butyl-5-(1-hydroxy-cyclohexyl)-5- phenyl-[1,3]dioxolan-4-one (step Siii) with (2R,5S)-2-tert-butyl-5-(1-hydroxy-cyclopentyl)-5-phenyl-[1,3]dioxolan-4-one.

Tiii) (R)-Cyclopentyl-hydroxy-phenyl-acetic acid

This compound is prepared analogously to (S)-cyclohexyl-hydroxy-thiophen-2-yl-acetic acid (R)-(1-aza-bicyclo[2.2.2]oct-3-yl)ester by replacing (S)-cyclohexyl-hydroxy-thiophen-2-yl-acetic acid with (R)-cyclopentyl-hydroxy-phenyl-acetic acid.

Preparation of Specific Examples

Example 1

(R)-3-[2,2-Bis-(2-chloro-phenyl)-2-hydroxy-acetoxy]-1-(isoxazol-3-ylcarbamoylmethyl)-1-azonia-bicyclo[2.2.2]octane bromide To a stirred solution of bis-(2-chloro-phenyl)-hydroxy-acetic acid (0.17 g, 0.572 mmol) in dry DMF (3 ml) under an inert atmosphere of Argon is added CDI (0.097 g, 0.6 mmol). After 1 hour, (R)-3-hydroxy-1-(isoxazol-3-ylcarbamoylmethyl)-1-azonia-bicyclo[2.2.2]octane bromide (Intermediate A) (0.2 g, 0.602 mmol) is added and the reaction mixture is heated to 40° C. overnight. Purification using C-18 reverse phase column chromatography (eluent: water-acetonitrile) affords a solid which is triturated with diethyl ether to yield the titled compound as a crystalline solid.

Example 2

(R)-3-(2-Hydroxy-2,2-di-p-tolyl-acetoxy)-1-(isoxazol-3-ylcarbamoylmethyl)-1-azonia-bicyclo[2.2.2]octane bromide This compound is prepared analogously to (R)-3-[2,2-bis-(2-chloro-phenyl)-2-hydroxy-acetoxy]-1-(isoxazol-3-ylcarbamoylmethyl)-1-azonia-bicyclo[2.2.2]octane bromide [Example 1] by substituting bis-(2-chloro-phenyl)-hydroxy-acetic acid with hydroxy-di-p-tolyl-acetic acid (Intermediate B).

Example 3

(R)-3-[2-Hydroxy-2,2-bis-(4-methoxy-phenyl)-acetoxy]-1-(isoxazol-3-ylcarbamoyl methyl)-1-azonia-bicyclo[2.2.2]octane bromide This compound is prepared analogously to (R)-3-[2,2-bis-(2-chloro-phenyl)-2-hydroxy-acetoxy]-1-(isoxazol-3-ylcarbamoylmethyl)-1-azonia-bicyclo[2.2.2]octane bromide [Example 1] by substituting bis-(2-chloro-phenyl)-hydroxy-acetic acid with hydroxy-bis-(4-methoxy-phenyl)-acetic acid (Intermediate C).

Example 4

(R)-3-(2,2-Diphenyl-propionyloxy)-1-(isoxazol-3-ylcarbamoylmethyl)-1-azonia-bicyclo[2.2.2.]octane bromide To a stirred suspension of (R)-3-hydroxy-1-(isoxazol-3-ylcarbamoylmethyl)-1-azonia-bicyclo-[2.2.2]octane bromide (Intermediate A) (0.4 g, 1.2 mmol) in DMF (4 ml) under an inert atmosphere of Argon is added sodium hydride (0.096 g of a 60% dispersion in oil, 2.4 mmol). The reaction mixture is stirred at room temperature for 2 hours during which time, a second reaction mixture comprising 2,2'-diphenylpropionic acid (0.129 g, 0.57 mmol) in DMF (2 ml) is prepared. To this is stirred solution is added CDI (0.097 g, 0.6 mmol). After stirring for 1.5 hours, the solution comprising the sodium salt of (R)-3-hydroxy-1-(isoxazol-3-ylcarbamoyl-methyl)-1-azonia-bicyclo[2.2.2]octane bromide is added and stirring continues for a further 3 hours. A mixture of hydrogen bromide (0.2 ml of a 48% aqueous solution) and water (3 ml) is added to the reaction mixture and purification is carried out using C-18 reverse phase column chromatography (eluent: water-acetonitrile) to yield the titled compound as a white solid.

Examples 5-12

These compounds namely, (R)-3-Diphenylacetoxy-1-(isoxazol-3-ylcarbamoylmethyl)-1-azonia-icyclo[2.2.2]octane bromide (Example 5), (R)-1-(Isoxazol-3-ylcarbamoyl-methyl)-3-(2-methoxy-2,2-diphenyl-acetoxy)-1-azonia-bicyclo[2.2.2]octane bromide (Example 6), (R)-3-(2-Ethylsulfanyl-2,2-diphenyl-acetoxy)-1-(isoxazol-3-ylcarbamoylmethyl)-1-azonia-bicyclo[2.2.2]octane bromide (Example 7), (R)-3-(2-Cyclohexyl-2-hydroxy-2-phenyl-acetoxy)-1-(isoxazol-3-ylcarbamoylmethyl)-1-azonia-bicyclo[2.2.2]octane bromide (Example 8) (mixture of R and S diastereomers at the hydroxyl position), (R)-3-(2-Cyclopentyl-2-hydroxy-2-thiophen-2-yl-acetoxy)-1-(isoxazol-3-ylcarbamoylmethyl)-1-azonia-bicyclo[2.2.2]octane bromide (Example 9) (mixture of R and S diastereomers at the hydroxyl position), (R)-3-(2-Cyclohexyl-2-hydroxy-2-thiophen-2-yl-acetoxy)-1-(isoxazol-3-ylcarbamoylmethyl)-1-azonia-bicyclo[2.2.2]octane bromide (Example 10) (mixture of R and S diastereomers at the hydroxyl position), (R)-3-(2-Cyclopentyl-2-hydroxy-2-phenyl-acetoxy)-1-(isoxazol-3-ylcarbamoyl-methyl)-1-azonia-bicyclo[2.2.2]octane bromide (Example 11)(mixture of R and S diastereomers at the hydroxyl position), (R)-3-(9-Hydroxy-(H-fluorene-9-carbonyloxy)-1-(isoxazol-3-ylcarbamoylmethyl)-1-azoina-bicyclo[2.2.2]octane bromide (Example 12) are prepared analogously to (R)-3-(2,2-Diphenyl-propionyloxy)-1-(isoxazol-3-ylcarbamoylmethyl)-1-azonia-bicyclo[2.2.2]octane bromide (Example 4) by replacing 2,2'-diphenylpropionic acid with the appropriate acid. For Examples 8 and 11, the mixture of diastereomers is separated by HPLC.

Example 13

(R)-3-(2-Hydroxy-2,2-diphenyl-acetoxy)-1-(5-methyl-isoxazol-3-ylcarbamoyl)-methyl-1-azonia-bicyclo[2.2.2]octane bromide The titled compound is prepared analogously to (R)-3-(2,2-diphenyl-propionyloxy)-1-(isoxazol-3-ylcarbamoylmethyl)-1-azonia-bicyclo[2.2.2]octane bromide (Example 4) by replacing (R)-3-hydroxy-1-(isoxazol-3-ylcarbamoylmethyl)-1-azonia-bicyclo[2.2.2]octane bromide (Intermediate A) with (R)-3-hydroxy-1-[(5-methyl-isoxazol-3-ylcarbamoyl)-methyl]-1-azonia-bicyclo[2.2.2]octane bromide (Intermediate F) and by replacing 2,2'-diphenylpropionic acid with hydroxy-diphenyl-acetic acid. $M^+$ 476.4

Example 14

(R)-3-(2-Hydroxy-2,2-diphenyl-avetoxy)-1-[1(isoxazol-3-ylcarbamoyl)-ethyl]-1-azonia-bicyclo[2.2.2]octane bromide This compound is prepared analogously to (R)-3-(2,2-diphenyl-propionyloxy)-1-(isoxazol-3-ylcarbamoylmethyl)-

1-azonia-bicyclo[2.2.2]octane bromide [Example 4] by replacing (R)-3-hydroxy-1-(isoxazol-3-ylcarbamoylmethyl)-1-azonia-bicyclo[2.2.2]octane bromide (Intermediate A) with (R)-3-hydroxy-1-[1-(isoxazol-3-ylcarbamoyl)-ethyl]-1-azonia-bicyclo[2.2.2]octane bromide (Intermediate G) and by replacing 2,2'-diphenylpropionic acid with hydroxy-diphenyl-acetic acid. (A diastereomeric mixture is obtained). M+ 476.6

Example 15

(R)-3-(2-Cyclopentyl-2-hydroxy-2-phenyl-acetoxy)-1-(pyrazin-2-ylcarbamoylmethyl)-1-azonia-bicyclo[2.2.2]octane bromide This compound is prepared analogously to (R)-3-(2,2-Diphenyl-propionyloxy)-1-(isoxazol-3-ylcarbamoylmethyl)-1-azonia-bicyclo[2.2.2]octane bromide (Example 4), substituting (R)-3-hydroxy-1-(isoxazol-3-ylcarbamoylmethyl)-1-azonia-bicyclo[2.2.2]octane bromide (Intermediate A) with (R)-3-Hydroxy-1-(pyrazin-2-ylcarbamoylmethyl)-1-azonia-bicyclo[2.2.2]octane bromide (Intermediate H) and by replacing 2,2'-diphenylpropionic acid with cyclopentyl-hydroxy-phenyl-acetic acid, yielding the titled compound as a diastereomeric mixture. (M+ 465.4)

Example 16

(R)-3-(2-Cyclohexyl-2-hydroxy-2-phenyl-acetoxy)-1-(pyrimidin-4-ylcarbamoylmethyl)-1-azonia-bicyclo[2.2.2]octane bromide This compound is prepared analogously to (R)-3-(2-Cyclopentyl-2-hydroxy-2-phenyl-acetoxy)-1-(pyrazin-2-ylcarbamoylmethyl)-1-azonia-bicyclo[2.2.2]octane bromide (Example 15) by replacing (R)-3-Hydroxy-1-(pyrazin-2-ylcarbamoylmethyl)-1-azonia-bicyclo-[2.2.2]octane bromide (Intermediate H) with (R)-3-Hydroxy-1-(pyrimidin-4-ylcarbamoyl-methyl)-1-azonia-bicyclo[2.2.2]octane bromide (Intermediate Q) and by replacing cyclopentyl-hydroxy-phenyl-acetic acid with cyclohexyl-hydroxy-phenyl-acetic acid, yielding the titled compound as a diastereomeric mixture. (M+ 479.5).

Example 17

(R)-3-(2-Cyclohexyl-2-hydroxy-2-phenyl-acetoxy)-1-[(4-phenyl-isoxazol-3-ylcarbamoyl)-methyl]-1-azonia-bicyclo[2.2.2]octane bromide This compound is prepared analogously to (R)-3-(2,2-diphenyl-propionyloxy)-1-(isoxazol-3-ylcarbamoylmethyl)-1-azonia-bicyclo[2.2.2]octane bromide (Example 4), substituting (R)-3-hydroxy-1-(isoxazol-3-ylcarbamoylmethyl)-1-azonia-bicyclo[2.2.2]octane bromide (Intermediate A) with (R)-3-hydroxy-1-[(4-phenyl-isoxazol-3-ylcarbamoyl)-methyl]-1-azonia-bicyclo[2.2.2]octane bromide (Intermediate I) and by replacing 2,2'-diphenylpropionic acid with cyclohexyl-hydroxy-phenyl-acetic acid, yielding the titled compound as a diastereomeric mixture. (M+ 544.4)

Example 18

3-[2-Hydroxy-2,2-bis-(3-methoxy-phenyl)-acetoxy]-1-(isoxazol-3-ylcarbamoylmethyl)-1-azonia-bicyclo[2.2.2]octane bromide To a stirred solution of hydroxy-bis-(3-methoxy-phenyl)-acetic acid (R)-(1-aza-bicyclo[2.2.2]-oct-3-yl)ester (Intermediate K) (0.25 g, 0.63 mmol) in acetonitrile (10 ml) is added 2-bromo-N-isoxazol-3-yl-acetamide (0.15 g, 0.73 mmol) and the reaction mixture stirred at room temperature for 3 hours. The resulting precipitate is removed by filtration and the mother liquor is left at room temperature for 72 hours to crystallise. The crystals are filtered and dried in vacuo to yield the titled compound as a solid.

Example 19

(R)-3-(2-Cyclopentyl-2-hydroxy-2-thiophen-2-yl-acetoxy)-1-(pyrazin-2-ylcarbamoylmethyl)-1-azonia-bicyclo[2.2.2]octane bromide This compound is prepared using a method analogous to Example 4, replacing (R)-3-hydroxy-1-(isoxazol-3-ylcarbamoylmethyl)-1-azonia-bicyclo[2.2.2]octane bromide (Intermediate A) with (R)-3-Hydroxy-1-(pyrazin-2-ylcarbamoylmethyl)-1-azonia-bicyclo[2.2.2]octane bromide (Intermediate H) and 2,2'-diphenylpropionic acid with cyclopentyl-H-hydroxy-thiophen-2-yl-acetic acid (Intermediate D).

Example 20

(R)-3-(2-Cyclohexyl-2-hydroxy-2-phenyl-acetoxy)-1-(pyrazin-2-ylcarbamoylmethyl)-1-azonia-bicyclo[2.2.2]octane bromide (Diastereomeric Mixture)

This compound is prepared as a diastereomeric mixture using an method analogous to Example 4, by replacing (R)-3-hydroxy-1-(isoxazol-3-ylcarbamoylmethyl)-1-azonia-bicyclo[2.2.2]octane bromide (Intermediate A) with (R)-3-Hydroxy-1-(pyrazin-2-ylcarbamoylmethyl)-1-azonia-bicyclo[2.2.2]octane bromide (Intermediate H) and 2,2'-diphenylpropionic acid with cyclohexyl-hydroxy-phenyl-acetic acid.

Example 21

(R)-3-(2-Cyclopentyl-2-hydroxy-2-phenyl-acetoxy)-1-(pyrazin-2-ylcarbamoylmethyl)-1-azonia-bicyclo[2.2.2]octane bromide This compound is prepared using an method analogous to Example 4 by replacing (R)-3-hydroxy-1-(isoxazol-3-ylcarbamoylmethyl)-1-azonia-bicyclo[2.2.2]octane bromide (Intermediate A) with (R)-3-Hydroxy-1-(pyrazin-2-ylcarbamoylmethyl)-1-azonia-bicyclo[2.2.2]octane bromide (Intermediate H) and 2,2'-diphenylpropionic acid with cyclopentyl-hydroxy-phenyl-acetic acid.

Example 22

(R)-3-[2-Hydroxy-2-(4-methoxy-phenyl)-2-phenyl-acetoxy]-1-(isoxazol-3-ylcarbamoylmethyl)-1-azonia-bicyclo[2.2.2]octane bromide To a stirred solution of bromo-N-isoxazol-3-yl-acetamide (Intermediate Ai) (0.057 g, 0.278 mmol) in dry chloroform (1 ml) heated to 50° C. is added hydroxy-(4-methoxy-phenyl)-phenyl-acetic acid (R)-(1-aza-bicyclo[2.2.2]oct-3-yl)ester (Intermediate O) in chloroform (1 ml). The reaction mixture is stirred at 50° C. for 6 hours after which time, the titled product is detected by LC-MS. (M+ 492.3)

Example 23

(R)-3-(2-Hydroxy-2-phenyl-2-o-tolyl-acetoxy)-1-(isoxazol-3-ylcarbamoylmethyl)-1-azonia-bicyclo[2.2.2]octane bromide This compound is prepared using an method analogous to (R)-3-[2-hydroxy-2-(4-methoxy-phenyl)-2-phenyl-acetoxy]-1-(isoxazol-3-ylcarbamoylmethyl)-1-azonia-bicyclo[2.2.2]-octane bromide (Example 22) by replacing hydroxy-(4-methoxy-phenyl)-phenyl-acetic acid (R)-(1-aza-bicyclo[2.2.2]oct-3-yl)ester (Intermediate O) with hydroxy-phenyl-o-tolyl-acetic acid (R)-(1-aza-bicyclo[2.2.2]oct-3-yl)ester (Intermediate P).

Example 24

(R)-3-[2-Hydroxy-2-(2-methoxy-phenyl)-2-phenyl-acetoxy]-1-(isoxazol-3-ylcarbamoylmethyl)-1-azonia-bicyclo[2.2.2]octane bromide This compound is prepared analogously to (R)-3-[2,2-bis-(2-chloro-phenyl)-2-hydroxy-acetoxy]-1-(isoxazol-3-ylcarbamoylmethyl)-1-azonia-bicyclo[2.2.2]octane bromide [Example 1] by substituting bis-(2-chloro-phenyl)-hydroxy-acetic acid with Hydroxy-(2-methoxy-phenyl)-phenyl-acetic acid (Intermediate N).

Examples 25-27

These compounds namely, (R)-3-(2-Cyclopentyl-2-hydroxy-2-phenyl-acetoxy)-1-(pyrimidin-4-ylcarbamoylmethyl)-1-azonia-bicyclo[2.2.2]octane bromide, (R)-3-(2-Cyclopentyl-2-hydroxy-2-thiophen-2-yl-acetoxy)-1-(pyrimidin-4-yl carbamoylmethyl)-1-azonia-bicyclo[2.2.2]octane bromide and (R)-3-(2-Cyclohexyl-2-hydroxy-2-thiophen-2-yl-acetoxy)-1-(pyrimidin-4-yl-carbamoylmethyl)-1-azonia-bicyclo[2.2.2]octane bromide are prepared analogously to (R)-3-(2,2-Diphenyl-propionyloxy)-1-(isoxazol-3-ylcarbamoylmethyl)-1-azonia-bicyclo[2.2.2]octane bromide (see Example 4) by replacing (R)-3-hydroxy-1-(isoxazol-3-ylcarbamoylmethyl)-1-azonia-bicyclo[2.2.2]octane bromide (Intermediate A) with (R)-3-Hydroxy-1-(pyrimidin-4-ylcarbamoylmethyl)-1-azonia-bicyclo[2.2.2]octane bromide and by replacing 2,2'-diphenyl-propionic acid with the appropriate acid.

Example 28

(R)-3-(2-Cyclopentyl-2-furan-2-yl-2-hydroxy-acetoxy)-1-(isoxazol-3-ylcarbamoylmethyl)-1-azonia-bicyclo[2.2.2]octane bromide This compound is prepared analogously to (R)-3-(2,2-Diphenyl-propionyloxy)-1-(isoxazol-3-ylcarbamoylmethyl)-1-azonia-bicyclo[2.2.2]octane bromide (See Example 4) by replacing 2,2'-diphenylpropionic acid with cyclopentyl-furan-2-yl-hydroxy-acetic acid.

Example 29

(R)-3-((S)-2-Cyclohexyl-2-hydroxy-2-thiophen-2-yl-acetoxy)-1-(isoxazol-3-ylcarbamoylmethyl)-1-azonia-bicyclo[2.2.2]octane phosphate To a solution comprising (S)-cyclohexyl-hydroxy-thiophen-2-yl-acetic acid (R)-(1-aza-bicyclo-[2.2.2]oct-3-yl) ester (Intermediate R) (105.6 g, 0.302 mol) in THF (1.8 litres) is added 2-bromo-N-isoxazol-3-yl-acetamide (Intermediate Ai) (61.9 g, 0.302 mol) in one portion. The reaction mixture is stirred at room temperature for 2 hours and then water (690 ml) is added to the gel-like mixture to dissolve the product which is present as the bromide salt. The bromide is converted 'in-situ' to the phosphate via ion exchange chromatography eluting with THF/water (2.6:1) using Ambersep-900-OH resin which is pre-treated with phosphoric acid. The fractions are collected and concentrated in vacuo to remove the organic solvent and the titled product is obtained by recrystallisation from the cooled aqueous liquor.

The compound is shown to be >98% chirally pure by the following method:

The compound (1 mg) is dissolved in acetonitrile (200 μl), water (700 μl), phosphate buffer (700 μl) and PTS marker (20 μl). It is then loaded onto a PACE MDQ CE column under the following conditions:

| | |
|---|---|
| Capillary: | 50 mm × 50u fused silica. |
| Run Buffer: | 5% w/v highly sulphated gamma cyclodextrin in 50/50 water/phosphate buffer (pH 2.5) |
| Cartridge temp: | 22 C. |
| Detector wavelength: | 214 nm |
| Events: | |
| Rinse-pressure 20 psi | 4.0 min fwd |
| Inject-pressure 0.3 psi | 4.0 sec fwd |
| Wait | 0.0 min |
| Separate-voltage | 20 Kv 15.00 min 0.17 min ramp. Reverse polarity |
| Wait | 0.0 min |

The compound retention time is 8.454 min.

Examples 30 and 31

These compounds namely, (R)-3-((R)-2-cyclohexyl-2-hydroxy-2-phenyl-acetoxy)-1-(isoxazol-3-ylcarbamoylmethyl)-1-azonia-bicyclo[2.2.2]octane phosphate (retention time on CE column under the same conditions as those described above=9.663 min) (Example 30, R isomer of Example 8) and (R)-3-((R)-2-cyclopentyl-2-hydroxy-2-phenyl-acetoxy)-1-(isoxazol-3-yl-carbamoylmethyl)-1-azonia-bicyclo[2.2.2]octane phosphate (retention time on CE column under the same conditions as those described above=8.863 min) (Example 31, R isomer of Example 11) are prepared analogously to (R)-34(S)-2-cyclohexyl-2-hydroxy-2-thiophen-2-yl-acetoxy)-1-(isoxazol-3-ylcarbamoylmethyl)-1-azonia-bicyclo[2.2.2]octane phosphate (Example 29) by replacing (S)-cyclohexyl-hydroxy-thiophen-2-yl-acetic acid (R)-(1-aza-bicyclo[2.2.2]oct-3-yl)ester (Intermediate R) with the appropriate ester the preparation of which is described herein.

Examples 32 to 54

The following compounds can be made analogously to Example 1 or as detailed previously in the experimental section:

(R)-3-[2-(2-Chloro-phenyl)-2-hydroxy-2-phenyl-acetoxy]-1-(isoxazol-3-ylcarbamoylmethyl)-1-azonia-bicyclo[2.2.2]octane bromide, (R)-3-(2-Cyclopropyl-2-hydroxy-2-thiophen-2-yl-acetoxy)-1-(isoxazol-3-ylcarbamoylmethyl)-1-azonia-bicyclo[2.2.2]octane bromide, (R)-3-(2-Cyclobutyl-2-hydroxy-2-thiophen-2-yl-acetoxy)-1-(isoxazol-3-ylcarbamoylmethyl)-1-azonia-bicyclo[2.2.2]octane bromide, (R)-3-(2-Cyclohexyl-2-hydroxy-2-thiophen-3-yl-acetoxy)-1-(isoxazol-3-ylcarbamoylmethyl)-1-azonia-bicyclo[2.2.2]octane bromide,
(R)-3-(2-Cyclopentyl-2-hydroxy-2-thiophen-3-yl-acetoxy)-1-(isoxazol-3-ylcarbamoylmethyl)-1-azonia-bicyclo[2.2.2]octane bromide,
(R)-3-(2-Hydroxy-2,2-di-thiophen-3-yl-acetoxy)-1-(isoxazol-3-ylcarbamoylmethyl)-1-azonia-bicyclo[2.2.2]octane bromide,
(R)-3-(2-Hydroxy-2-phenyl-2-thiophen-3-yl-acetoxy)-1-(isoxazol-3-ylcarbamoylmethyl)-1-azonia-bicyclo[2.2.2]octane bromide,
(R)-3-[2-(3,3-Difluoro-cyclopentyl)-2-hydroxy-2-phenyl-acetoxy]-1-(isoxazol-3-ylcarbamoyl-methyl)-1-azonia-bicyclo[2.2.2]octane bromide,
(R)-3-[2-(3,3-Difluoro-cyclopentyl)-2-hydroxy-2-thiophen-2-yl-acetoxy]-1-(isoxazol-3-yl-carbamoylmethyl)-1-azonia-bicyclo[2.2.2]octane bromide,
(R)-3-[2-(3,3-Difluoro-cyclopentyl)-2-hydroxy-2-thiophen-3-yl-acetoxy]-1-(isoxazol-3-yl-carbamoylmethyl)-1-azonia-bicyclo[2.2.2]octane bromide,
(R)-3-(9H-Fluorene-9-carbonyloxy)-1-(isoxazol-3-ylcarbamoylmethyl)-1-azonia-bicyclo[2.2.2]-octane bromide,
(R)-3-(9,10-Dihydro-anthracene-9-carbonyloxy)-1-(isoxazol-3-ylcarbamoylmethyl)-1-azonia-bicyclo[2.2.2]octane bromide,
(R)-1-(Isoxazol-3-ylcarbamoylmethyl)-3-(9H-xanthene-9-carbonyloxy)-1-azonia-bicyclo[2.2.2]-octane bromide,
(R)-3-(2-Cyclopentyl-2-furan-2-yl-2-hydroxy-acetoxy)-1-(isoxazol-3-ylcarbamoylmethyl)-1-azonia-bicyclo[2.2.2]octane bromide,
(R)-3-(2-Cyclohexyl-2-furan-3-yl-2-hydroxy-acetoxy)-1-(isoxazol-3-ylcarbamoylmethyl)-1-azonia-bicyclo[2.2.2]octane bromide,
(R)-3-(2-Cyclopentyl-2-furan-3-yl-2-hydroxy-acetoxy)-1-(isoxazol-3-ylcarbamoylmethyl)-1-azonia-bicyclo[2.2.2]octane bromide,
(R)-3-(2-Furan-3-yl-2-hydroxy-2-phenyl-acetoxy)-1-(isoxazol-3-ylcarbamoylmethyl)-1-azonia-bicyclo[2.2.2]octane bromide,
(R)-3-(2,2-Di-furan-3-yl-2-hydroxy-acetoxy)-1-(isoxazol-3-ylcarbamoylmethyl)-1-azonia-bicyclo[2.2.2]octane bromide,
(R)-3-(2,2-Dicyclopentyl-2-hydroxy-acetoxy)-1-(isoxazol-3-ylcarbamoylmethyl)-1-azonia-bicyclo[2.2.2]octane bromide,
(R)-3-(2,2-Dicyclohexyl-2-hydroxy-acetoxy)-1-(isoxazol-3-ylcarbamoylmethyl)-1-azonia-bicyclo[2.2.2]octane bromide,
(R)-3-(9-Hydroxy-9H-xanthene-9-carbonyloxy)-1-(isoxazol-3-ylcarbamoylmethyl)-1-azonia-bicyclo[2.2.2]octane bromide,
(R)-3-(9-Hydroxy-9,10-dihydro-anthracene-9-carbonyloxy)-1-(isoxazol-3-ylcarbamoylmethyl)-1-azonia-bicyclo[2.2.2]octane bromide, and
(R)-3-(5-Hydroxy-5H-dibenzo[a,d]cycloheptene-5-carbonyloxy)-1-(isoxazol-3-ylcarbamoyl-methyl)-1-azonia-bicyclo[2.2.2]octane bromide Examples 55 to 76

The following compounds can be made analogously to Example 16 or as detailed previously in the experimental section:
(R)-3-(2-Cyclohexyl-2-furan-2-yl-2-hydroxy-acetoxy)-1-(pyrimidin-4-ylcarbamoylmethyl)-1-azonia-bicyclo[2.2.2]octane bromide,
(R)-3-(2-Cyclopentyl-2-furan-2-yl-2-hydroxy-acetoxy)-1-(pyrimidin-4-ylcarbamoylmethyl)-1-azonia-bicyclo[2.2.2]octane bromide,
(R)-3-(2-Cyclopentyl-2-furan-3-yl-2-hydroxy-acetoxy)-1-(pyrimidin-4-ylcarbamoylmethyl)-1-azonia-bicyclo[2.2.2]octane bromide,
(R)-3-(2-Cyclohexyl-2-furan-3-yl-2-hydroxy-acetoxy)-1-(pyrimidin-4-ylcarbamoylmethyl)-1-azonia-bicyclo[2.2.2]octane bromide,
(R)-3-(2-Furan-3-yl-2-hydroxy-2-phenyl-acetoxy)-1-(pyrimidin-4-ylcarbamoylmethyl)-1-azonia-bicyclo[2.2.2]octane bromide,
(R)-3-(2,2-Di-furan-3-yl-2-hydroxy-acetoxy)-1-(pyrimidin-4-ylcarbamoylmethyl)-1-azonia-bicyclo[2.2.2]octane bromide,
(R)-3-(2-Cyclohexyl-2-hydroxy-2-thiophen-3-yl-acetoxy)-1-(pyrimidin-4-ylcarbamoylmethyl)-1-azonia-bicyclo[2.2.2]octane bromide,
(R)-3-(2-Cyclopentyl-2-hydroxy-2-thiophen-3-yl-acetoxy)-1-(pyrimidin-4-ylcarbamoylmethyl)-1-azonia-bicyclo[2.2.2]octane bromide,
(R)-3-(2-Hydroxy-2,2-di-thiophen-3-yl-acetoxy)-1-(pyrimidin-4-ylcarbamoylmethyl)-1-azonia-bicyclo[2.2.2]octane bromide,
(R)-3-(2-Hydroxy-2-phenyl-2-thiophen-3-yl-acetoxy)-1-(pyrimidin-4-ylcarbamoylmethyl)-1-azonia-bicyclo[2.2.2]octane bromide,
(R)-3-(2,2-Dicyclopentyl-2-hydroxy-acetoxy)-1-(pyrimidin-4-ylcarbamoylmethyl)-1-azonia-bicyclo[2.2.2]octane bromide,
(R)-3-(2,2-Dicyclohexyl-2-hydroxy-acetoxy)-1-(pyrimidin-4-ylcarbamoylmethyl)-1-azonia-bicyclo[2.2.2]octane bromide,
(R)-3-[2-(3,3-Difluoro-cyclopentyl)-2-hydroxy-2-phenyl-acetoxy]-1-(pyrimidin-4-ylcarbamoyl-methyl)-1-azonia-bicyclo[2.2.2]octane bromide,
(R)-3-(9-Hydroxy-9H-fluorene-9-carbonyloxy)-1-(pyrimidin-4-ylcarbamoylmethyl)-1-azonia-bicyclo[2.2.2]octane bromide,
(R)-3-(9H-Fluorene-9-carbonyloxy)-1-(pyrimidin-4-ylcarbamoylmethyl)-1-azonia-bicyclo-[2.2.2]octane bromide,
(R)-3-(9,10-Dihydro-anthracene-9-carbonyloxy)-1-(pyrimidin-4-ylcarbamoylmethyl)-1-azonia-bicyclo[2.2.2]octane bromide,
(R)-1-(Pyrimidin-4-ylcarbamoylmethyl)-3-(9H-xanthene-9-carbonyloxy)-1-azonia-bicyclo-[2.2.2]octane bromide,
(R)-3-[2-(3,3-Difluoro-cyclopentyl)-2-hydroxy-2-thiophen-2-yl-acetoxy]-1-(pyrimidin-4-yl-carbamoylmethyl)-1-azonia-bicyclo[2.2.2]octane bromide,
(R)-3-[2-(3,3-Difluoro-cyclopentyl)-2-hydroxy-2-thiophen-3-yl-acetoxy]-1-(pyrimidin-4-yl-carbamoylmethyl)-1-azonia-bicyclo[2.2.2]octane bromide,
(R)-3-(-(9-Hydroxy-9H-xanthene-9-carbonyloxy)-1-(pyrimidin-4-ylcarbamoylmethyl)-1-azonia-bicyclo[2.2.2]octane bromide,
(R)-3-(9-Hydroxy-9,10-dihydro-anthracene-9-carbonyloxy)-1-(pyrimidin-4-ylcarbamoyl-methyl)-1-azonia-bicyclo[2.2.2]octane bromide, and
(R)-3-(5-Hydroxy-5H-dibenzo[a,d]cycloheptene-5-carbonyloxy)-1-(pyrimidin-4-ylcarbamoyl-methyl)-1-azonia-bicyclo[2.2.2]octane bromide.

Examples 77 to 102

The following compounds can be made analogously to Example 15 or as detailed previously in the experimental section:

(R)-3-(2-Cyclohexyl-2-furan-2-yl-2-hydroxy-acetoxy)-1-(pyrimidin-2-ylcarbamoylmethyl)-1-azonia-bicyclo[2.2.2]octane bromide,
(R)-3-(2-Cyclopentyl-2-furan-2-yl-2-hydroxy-acetoxy)-1-(pyrimidin-2-ylcarbamoylmethyl)-1-azonia-bicyclo[2.2.2]octane bromide,
(R)-3-(2-Cyclopentyl-2-furan-3-yl-2-hydroxy-acetoxy)-1-(pyrimidin-2-ylcarbamoylmethyl)-1-azonia-bicyclo[2.2.2]octane bromide,
(R)-3-(2-Cyclohexyl-2-furan-3-yl-2-hydroxy-acetoxy)-1-(pyrimidin-2-ylcarbamoylmethyl)-1-azonia-bicyclo[2.2.2]octane bromide,
(R)-3-(2-Furan-3-yl-2-hydroxy-2-phenyl-acetoxy)-1-(pyridin-2-ylcarbamoylmethyl)-1-zonia-bicyclo[2.2.2]octane bromide,
(R)-3-(2,2-Di-furan-3-yl-2-hydroxy-acetoxy)-1-(pyrimidin-2-ylcarbamoylmethyl)-1-azonia-bicyclo[2.2.2]octane bromide,
(R)-3-(2-Cyclohexyl-2-hydroxy-2-thiophen-3-yl-acetoxy)-1-(pyrimidin-2-ylcarbamoylmethyl)-1-azonia-bicyclo[2.2.2]octane bromide,
(R)-3-(2-Cyclopentyl-2-hydroxy-2-thiophen-3-yl-acetoxy)-1-(pyrimidin-2-ylcarbamoylmethyl)-1-azonia-bicyclo[2.2.2]octane bromide,
(R)-3-(2-Hydroxy-2,2-di-thiophen-3-yl-acetoxy)-1-(pyrimidin-2-ylcarbamoylmethyl)-1-azonia-bicyclo[2.2.2]octane bromide,
(R)-3-(2-Hydroxy-2-phenyl-2-thiophen-3-yl-acetoxy)-1-(pyrimidin-2-ylcarbamoylmethyl)-1-azonia-bicyclo[2.2.2]octane bromide,
(R)-3-(2,2-Dicyclopentyl-2-hydroxy-acetoxy)-1-(pyrimidin-2-ylcarbamoylmethyl)-1-azonia-bicyclo[2.2.2]octane bromide,
(R)-3-(2,2-Dicyclohexyl-2-hydroxy-acetoxy)-1-(pyrimidin-2-ylcarbamoylmethyl)-1-azonia-bicyclo[2.2.2]octane bromide,
(R)-3-[2-(3,3-Difluoro-cyclopentyl)-2-hydroxy-2-phenyl-acetoxy]-1-(pyrimidin-4-ylcarbamoyl-methyl)-1-azonia-bicyclo[2.2.2]octane bromide,
(R)-3-(9-Hydroxy-9H-fluorene-9-carbonyloxy)-1-(pyrimidin-2-ylcarbamoylmethyl)-1-azonia-bicyclo[2.2.2]octane bromide,
(R)-3-(9H-Fluorene-9-carbonyloxy)-1-(pyrimidin-2-ylcarbamoylmethyl)-1-azonia-bicyclo-[2.2.2]octane bromide,
(R)-3-(9,10-Dihydro-anthracene-9-carbonyloxy)-1-(pyrimidin-2-ylcarbamoylmethyl)-1-azonia-bicyclo[2.2.2]octane bromide,
(R)-1-(Pyrimidin-2-ylcarbamoylmethyl)-3-(9H-xanthene-9-carbonyloxy)-1-azonia-bicyclo-[2.2.2]octane bromide,
(R)-3-[2-(3,3-Difluoro-cyclopentyl)-2-hydroxy-2-thiophen-2-yl-acetoxy]-1-(pyrimidin-2-yl-carbamoylmethyl)-1-azonia-bicyclo[2.2.2]octane bromide,
(R)-3-[2-(3,3-Difluoro-cyclopentyl)-2-hydroxy-2-thiophen-3-yl-acetoxy]-1-(pyrimidin-2-yl-carbamoylmethyl)-1-azonia-bicyclo[2.2.2]octane bromide,
(R)-3-(2-Cyclopentyl-2-hydroxy-2-thiophen-2-yl-acetoxy)-1-(pyrimidin-2-ylcarbamoylmethyl)-1-azonia-bicyclo[2.2.2]octane bromide,
(R)-3-(2-Cyclohexyl-2-hydroxy-2-thiophen-2-yl-acetoxy)-1-(pyrimidin-2-ylcarbamoylmethyl)-1-azonia-bicyclo[2.2.2]octane bromide,
(R)-3-(2-Cyclohexyl-2-hydroxy-2-phenyl-acetoxy)-1-(pyrimidin-2-ylcarbamoylmethyl)-1-azonia-bicyclo[2.2.2]octane bromide,
(R)-3-(2-Cyclopentyl-2-hydroxy-2-phenyl-acetoxy)-1-(pyrimidin-2-ylcarbamoylmethyl)-1-azonia-bicyclo[2.2.2]octane bromide,
(R)-3-(9-Hydroxy-9,10-dihydro-anthracene-9-carbonyloxy)-1-(pyridin-2-ylcarbamoylmethyl)-1-azonia-bicyclo[2.2.2]octane bromide,
(R)-3-(9-Hydroxy-9H-xanthene-9-carbonyloxy)-1-(pyridin-2-ylcarbamoylmethyl)-1-azonia-bicyclo[2.2.2]octane bromide, and
(R)-3-(5-Hydroxy-5H-dibenzo[a,d]cycloheptene-5-carbonyloxy)-1-(pyridin-2-ylcarbamoyl-methyl)-1-azonia-bicyclo[2.2.2]octane bromide, Examples 103 to 129

The following compounds can be made analogously to Example 15 or as detailed previously in the experimental section:

(R)-3-(2-Cyclohexyl-2-furan-2-yl-2-hydroxy-acetoxy)-1-(pyridazin-3-ylcarbamoyl)-1-azonia-bicyclo[2.2.2]octane bromide,
(R)-3-(2-Cyclopentyl-2-furan-2-yl-2-hydroxy-acetoxy)-1-(pyridazin-3-ylcarbamoyl)-1-azonia-bicyclo[2.2.2]octane bromide,
(R)-3-(2-Cyclohexyl-2-furan-3-yl-2-hydroxy-acetoxy)-1-(pyridazin-3-ylcarbamoyl)-1-azonia-bicyclo[2.2.2]octane bromide,
(R)-3-(2-Cyclopentyl-2-furan-3-yl-2-hydroxy-acetoxy)-1-(pyridazin-3-ylcarbamoyl)-1-azonia-bicyclo[2.2.2]octane bromide,
(R)-3-(2,2-Di-furan-3-yl-2-hydroxy-acetoxy)-1-(pyridazin-3-ylcarbamoyl)-1-azonia-bicyclo-[2.2.2]octane bromide,
(R)-3-(2-Furan-3-yl-2-hydroxy-2-phenyl-acetoxy)-1-(pyridazin-3-ylcarbamoyl)-1-azonia-bicyclo[2.2.2]octane bromide,
(R)-3-(2-Cyclohexyl-2-hydroxy-2-thiophen-3-yl-acetoxy)-1-(pyridazin-3-ylcarbamoyl)-1-azonia-bicyclo[2.2.2]octane bromide,
(R)-3-(2-Cyclopentyl-2-hydroxy-2-thiophen-3-yl-acetoxy)-1-(pyridazin-3-ylcarbamoyl)-1-azonia-bicyclo[2.2.2]octane bromide,
(R)-3-(2-Hydroxy-2,2-di-thiophen-3-yl-acetoxy)-1-(pyridazin-3-ylcarbamoyl)-1-azonia-bicyclo[2.2.2]octane bromide,
(R)-3-(2-Hydroxy-2-phenyl-2-thiophen-3-yl-acetoxy)-1-(pyridazin-3-ylcarbamoyl)-1-azonia-bicyclo[2.2.2]octane bromide,
(R)-3-(2,2-Dicyclopentyl-2-hydroxy-acetoxy)-1-(pyridazin-3-ylcarbamoyl)-1-azonia-bicyclo-[2.2.2]octane bromide,
(R)-3-(2,2-Dicyclohexyl-2-hydroxy-acetoxy)-1-(pyridazin-3-ylcarbamoyl)-1-azonia-bicyclo-[2.2.2]octane bromide,
(R)-3-(2-Cyclopentyl-2-hydroxy-2-thiophen-2-yl-acetoxy)-1-(pyridazin-3-ylcarbamoyl)-1-azonia-bicyclo[2.2.2]octane bromide,
(R)-3-(2-Cyclohexyl-2-hydroxy-2-thiophen-2-yl-acetoxy)-1-(pyridazin-3-ylcarbamoyl)-1-azonia-bicyclo[2.2.2]octane bromide,
(R)-3-[2-(3,3-Difluoro-cyclopentyl)-2-hydroxy-2-phenyl-acetoxy]-1-(pyridazin-3-ylcarbamoyl)-1-azonia-bicyclo[2.2.2]octane bromide,
(R)-3-(2-Cyclohexyl-2-hydroxy-2-phenyl-acetoxy)-1-(pyridazin-3-ylcarbamoyl)-1-azonia-bicyclo[2.2.2]octane bromide,
(R)-3-(2-Cyclopentyl-2-hydroxy-2-phenyl-acetoxy)-1-(pyridazin-3-ylcarbamoyl)-1-azonia-bicyclo[2.2.2]octane bromide,
(R)-3-(9-Hydroxy-9H-fluorene-9-carbonyloxy)-1-(pyridazin-3-ylcarbamoyl)-1-azonia-bicyclo-[2.2.2]octane bromide, (R)-3-(9-Hydroxy-9H-fluorene-9-carbonyloxy)-1-(pyridazin-3-ylcarbamoyl)-1-azonia-bicyclo-[2.2.2]octane bromide,
(R)-3-(9-Hydroxy-9H-xanthene-9-carbonyloxy)-1-(pyridazin-3-ylcarbamoyl)-1-azonia-bicyclo-[2.2.2]octane bromide,
(R)-3-(9-Hydroxy-9,10-dihydro-anthracene-9-carbonyloxy)-1-(pyridazin-3-ylcarbamoyl)-1-azonia-bicyclo[2.2.2]octane bromide,
(R)-3-(5-Hydroxy-5H-dibenzo[a,d]cycloheptene-5-carbonyloxy)-1-(pyridazin-3-ylcarbamoyl)-1-azonia-bicyclo[2.2.2]octane bromide.
(R)-3-[2-(3,3-Difluoro-cyclopentyl)-2-hydroxy-2-thiophen-2-yl-acetoxy]-1-(pyridazin-3-yl-carbamoyl)-1-azonia-bicyclo[2.2.2]octane bromide,
(R)-3-[2-(3,3-Difluoro-cyclopentyl)-2-hydroxy-2-thiophen-3-yl-acetoxy]-1-(pyridazin-3-yl-carbamoyl)-1-azonia-bicyclo[2.2.2]octane bromide,
(R)-3-(9H-Fluorene-9-carbonyloxy)-1-(pyridazin-3-ylcarbamoyl)-1-azonia-bicyclo[2.2.2]octane bromide,
(R)-3-(9,10-Dihydro-anthracene-9-carbonyloxy)-1-(pyridazin-3-ylcarbamoyl)-1-azonia-bicyclo-[2.2.2]octane bromide, and
(R)-1-(pyridazin-3-ylcarbamoyl)-3-(9H-xanthene-9-carbonyloxy)-1-azonia-bicyclo[2.2.2]octane bromide.

Examples 130 to 156

The following compounds can be made analogously to Example 15 or as detailed previously in the experimental section:
(R)-3-(2-Cyclopentyl-2-hydroxy-2-thiophen-2-yl-acetoxy)-1-([1,3,5]triazin-2-ylcarbamoyl-methyl)-1-azonia-bicyclo[2.2.2]octane bromide,
(R)-3-(2-Cyclohexyl-2-hydroxy-2-thiophen-2-yl-acetoxy)-1-([1,3,5]triazin-2-ylcarbamoyl-methyl)-1-azonia-bicyclo[2.2.2]octane bromide,
(R)-3-[2-(3,3-Difluoro-cyclopentyl)-2-hydroxy-2-phenyl-acetoxy]-1-([1,3,5]triazin-2-yl-carbamoylmethyl)-1-azonia-bicyclo[2.2.2]octane bromide,
(R)-3-(2-Cyclohexyl-2-hydroxy-2-phenyl-acetoxy)-1-([1,3,5]triazin-2-ylcarbamoylmethyl)-1-azonia-bicyclo[2.2.2]octane bromide,
(R)-3-(2-Cyclopentyl-2-hydroxy-2-phenyl-acetoxy)-1-([1,3,5]triazin-2-ylcarbamoylmethyl)-1-azonia-bicyclo[2.2.2]octane bromide,
(R)-3-(9-Hydroxy-9H-fluorene-9-carbonyloxy)-1-([1,3,5]triazin-2-ylcarbamoylmethyl)-1-azonia-bicyclo[2.2.2]octane bromide,
(R)-3-(2-Cyclohexyl-2-furan-2-yl-2-hydroxy-acetoxy)-1-([1,3,5]triazin-2-ylcarbamoylmethyl)-1-azonia-bicyclo[2.2.2]octane bromide,
(R)-3-(2-Cyclopentyl-2-furan-2-yl-2-hydroxy-acetoxy)-1-([1,3,5]triazin-2-ylcarbamoylmethyl)-1-azonia-bicyclo[2.2.2]octane bromide,
(R)-3-(2-Cyclohexyl-2-furan-3-yl-2-hydroxy-acetoxy)-1-([1,3,5]triazin-2-ylcarbamoylmethyl)-1-azonia-bicyclo[2.2.2]octane bromide,
(R)-3-(2-Cyclopentyl-2-furan-3-yl-2-hydroxy-acetoxy)-1-([1,3,5]triazin-2-ylcarbamoylmethyl)-1-azonia-bicyclo[2.2.2]octane bromide,
(R)-3-(2-Furan-3-yl-2-hydroxy-2-phenyl-acetoxy)-1-([1,3,5]triazin-2-ylcarbamoylmethyl)-1-azonia-bicyclo[2.2.2]octane bromide,
(R)-3-(2,2-Di-furan-3-yl-2-hydroxy-acetoxy)-1-([1,3,5]triazin-2-ylcarbamoylmethyl)-1-bicyclo[2.2.2]octane bromide,
(R)-3-(2-Cyclohexyl-2-hydroxy-2-thiophen-3-yl-acetoxy)-1-([1,3,5]triazin-2-ylcarbamoyl-methyl)-1-azonia-bicyclo[2.2.2]octane bromide,
(R)-3-(2-Cyclopentyl-2-hydroxy-2-thiophen-3-yl-acetoxy)-1-([1,3,5]triazin-2-ylcarbamoyl-methyl)-1-azonia-bicyclo[2.2.2]octane bromide,
(R)-3-(2-Hydroxy-2,2-di-thiophen-3-yl-acetoxy)-1-([1,3,5]triazin-2-ylcarbamoylmethyl)-1-azonia-bicyclo[2.2.2]octane bromide,
(R)-3-(2-Hydroxy-2-phenyl-2-thiophen-3-yl-acetoxy)-1-([1,3,5]triazin-2-ylcarbamoylmethyl)-1-azonia-bicyclo[2.2.2]octane bromide,
(R)-3-(2,2-Dicyclopentyl-2-hydroxy-acetoxy)-1-([1,3,5]triazin-2-ylcarbamoylmethyl)-1-azonia-bicyclo[2.2.2]octane bromide,
(R)-3-(2,2-Dicyclohexyl-2-hydroxy-acetoxy)-1-([1,3,5]triazin-2-ylcarbamoylmethyl)-1-azonia-bicyclo[2.2.2]octane bromide,
(R)-3-(9-Hydroxy-9H-fluorene-9-carbonyloxy)-1-([1,3,5]triazin-2-ylcarbamoylmethyl)-1-azonia-bicyclo[2.2.2]octane bromide,
(R)-3-(9-Hydroxy-9H-xanthene-9-carbonyloxy)-1-([1,3,5]triazin-2-ylcarbamoylmethyl)-1-azonia-bicyclo[2.2.2]octane bromide,
(R)-3-(9-Hydroxy-9,10-dihydro-anthracene-9-carbonyloxy)-1-([1,3,5]triazin-2-ylcarbamoyl-methyl)-1-azonia-bicyclo[2.2.2]octane bromide,
(R)-3-(5-Hydroxy-5H-dibenzo[a,d]cycloheptene-5-carbonyloxy)-1-([1,3,5]triazin-2-yl-carbamoylmethyl)-1-azonia-bicyclo[2.2.2]octane bromide,
(R)-3-[2-(3,3-Difluoro-cyclopentyl)-2-hydroxy-2-thiophen-2-yl-acetoxy]-1-([1,3,5]triazin-2-ylcarbamoylmethyl)-1-azonia-bicyclo[2.2.2]octane bromide,
(R)-3-[2-(3,3-Difluoro-cyclopentyl)-2-hydroxy-2-thiophen-3-yl-acetoxy]-1-([1,3,5]triazin-2-ylcarbamoylmethyl)-1-azonia-bicyclo[2.2.2]octane bromide,
(R)-3-(9H-Fluorene-9-carbonyloxy)-1-([1,3,5]triazin-2-ylcarbamoylmethyl)-1-azonia-bicyclo[2.2.2]octane bromide,
(R)-3-(9,10-Dihydro-anthracene-9-carbonyloxy)-1-([1,3,5]triazin-2-ylcarbamoylmethyl)-1-azonia-bicyclo[2.2.2]octane bromide, and
(R)-1-([1,3,5]triazin-2-ylcarbamoylmethyl)-3-(9H-xanthene-9-carbonyloxy)-1-azonia-bicyclo[2.2.2]octane bromide.

Examples 157 to 183

The following compounds can be made analogously to Example 16 or as detailed previously in the experimental section:
(R)-3-(2-Cyclopentyl-2-hydroxy-2-thiophen-2-yl-acetoxy)-1-(pyrimidin-5-ylcarbamoylmethyl)-1-azonia-bicyclo[2.2.2]octane bromide,
(R)-3-(2-Cyclohexyl-2-hydroxy-2-thiophen-2-yl-acetoxy)-1-(pyrimidin-5-ylcarbamoylmethyl)-1-azonia-bicyclo[2.2.2]octane bromide,
(R)-3-[2-(3,3-Difluoro-cyclopentyl)-2-hydroxy-2-phenyl-acetoxy]-1-(pyrimidin-5-ylcarbamoyl-methyl)-1-azonia-bicyclo[2.2.2]octane bromide,
(R)-3-(2-Cyclohexyl-2-hydroxy-2-phenyl-acetoxy)-1-(pyrimidin-5-ylcarbamoylmethyl)-1-azonia-bicyclo[2.2.2]octane bromide,
(R)-3-(2-Cyclopentyl-2-hydroxy-2-phenyl-acetoxy)-1-(pyrimidin-5-ylcarbamoylmethyl)-1-azonia-bicyclo[2.2.2]octane bromide, (R)-3-(9-Hydroxy-9H-fluorene-9-carbonyloxy)-1-(pyrimidin-5-ylcarbamoylmethyl)-1-azonia-bicyclo[2.2.2]octane bromide,
(R)-3-(2-Cyclohexyl-2-furan-2-yl-2-hydroxy-acetoxy)-1-(pyrimidin-5-ylcarbamoylmethyl)-1-azonia-bicyclo[2.2.2]octane bromide,
(R)-3-(2-Cyclopentyl-2-furan-2-yl-2-hydroxy-acetoxy)-1-(pyrimidin-5-ylcarbamoylmethyl)-1-azonia-bicyclo[2.2.2]octane bromide,
(R)-3-(2-Cyclohexyl-2-furan-3-yl-2-hydroxy-acetoxy)-1-(pyrimidin-5-ylcarbamoylmethyl)-1-azonia-bicyclo[2.2.2]octane bromide,
(R)-3-(2-Cyclopentyl-2-furan-3-yl-2-hydroxy-acetoxy)-1-(pyrimidin-5-ylcarbamoylmethyl)-1-azonia-bicyclo[2.2.2]octane bromide,
(R)-3-(2-Furan-3-yl-2-hydroxy-2-phenyl-acetoxy)-1-(pyrimidin-5-ylcarbamoylmethyl)-1-azonia-bicyclo[2.2.2]octane bromide,
(R)-3-(2,2-Di-furan-3-yl-2-hydroxy-acetoxy)-1-(pyrimidin-5-ylcarbamoylmethyl)-1-azonia-bicyclo[2.2.2]octane bromide,
(R)-3-(2-Cyclohexyl-2-hydroxy-2-thiophen-3-yl-acetoxy)-1-(pyrimidin-5-ylcarbamoylmethyl)-1-azonia-bicyclo[2.2.2]octane bromide,
(R)-3-(2-Cyclopentyl-2-hydroxy-2-thiophen-3-yl-acetoxy)-1-(pyrimidin-5-ylcarbamoylmethyl)-1-azonia-bicyclo[2.2.2]octane bromide,
(R)-3-(2-Hydroxy-2,2-di-thiophen-3-yl-acetoxy)-1-(pyrimidin-5-ylcarbamoylmethyl)-1-azonia-bicyclo[2.2.2]octane bromide,
(R)-3-(2-Hydroxy-2-phenyl-2-thiophen-3-yl-acetoxy)-1-(pyrimidin-5-ylcarbamoylmethyl)-1-azonia-bicyclo[2.2.2]octane bromide,
(R)-3-(2,2-Dicyclopentyl-2-hydroxy-acetoxy)-1-(pyrimidin-5-ylcarbamoylmethyl)-1-azonia-bicyclo[2.2.2]octane bromide,
(R)-3-(2,2-Dicyclohexyl-2-hydroxy-acetoxy)-1-(pyrimidin-5-ylcarbamoylmethyl)-1-azonia-bicyclo[2.2.2]octane bromide,
(R)-3-(9-Hydroxy-9H-fluorene-9-carbonyloxy)-1-(pyrimidin-5-ylcarbamoylmethyl)-1-azonia-bicyclo[2.2.2]octane bromide,
(R)-3-(9-Hydroxy-9H-xanthene-9-carbonyloxy)-1-(pyrimidin-5-ylcarbamoylmethyl)-1-azonia-bicyclo[2.2.2]octane bromide,
(R)-3-(9-Hydroxy-9,10-dihydro-anthracene-9-carbonyloxy)-1-(pyrimidin-5-ylcarbamoyl-methyl)-1-azonia-bicyclo[2.2.2]octane bromide,
(R)-3-(5-Hydroxy-5H-dibenzo[a,d]cycloheptene-5-carbonyloxy)-1-(pyrimidin-5-ylcarbamoyl-methyl)-1-azonia-bicyclo[2.2.2]octane bromide,
(R)-3-[2-(3,3-Difluoro-cyclopentyl)-2-hydroxy-2-thiophen-2-yl-acetoxy]-1-(pyrimidin-5-yl-carbamoylmethyl)-1-azonia-bicyclo[2.2.2]octane bromide,
(R)-3-[2-(3,3-Difluoro-cyclopentyl)-2-hydroxy-2-thiophen-3-yl-acetoxy]-1-(pyrimidin-5-yl-carbamoylmethyl)-1-azonia-bicyclo[2.2.2]octane bromide,
(R)-3-(9H-Fluorene-9-carbonyloxy)-1-(pyrimidin-5-ylcarbamoylmethyl)-1-azonia-bicyclo-[2.2.2]octane bromide,
(R)-3-(9,10-Dihydro-anthracene-9-carbonyloxy)-1-(pyrimidin-5-ylcarbamoylmethyl)-1-azonia-bicyclo[2.2.2]octane bromide, and
(R)-1-(pyrimidin-5-ylcarbamoylmethyl)-3-(9H-xanthene-9-carbonyloxy)-1-azonia-bicyclo-[2.2.2]octane bromide.

Examples 184 to 208

The following compounds can be made analogously to Example 15 or as detailed previously in the experimental section:

(R)-3-(2-Cyclohexyl-2-furan-2-yl-2-hydroxy-acetoxy)-1-(pyrazin-2-ylcarbamoylmethyl)-1-azonia-bicyclo[2.2.2]octane bromide,
(R)-3-(2-Cyclopentyl-2-furan-2-yl-2-hydroxy-acetoxy)-1-(pyrazin-2-ylcarbamoylmethyl)-1-azonia-bicyclo[2.2.2]octane bromide,
(R)-3-(2-Cyclohexyl-2-furan-3-yl-2-hydroxy-acetoxy)-1-(pyrazin-2-ylcarbamoylmethyl)-1-azonia-bicyclo[2.2.2]octane bromide,
(R)-3-(2-Cyclopentyl-2-furan-3-yl-2-hydroxy-acetoxy)-1-(pyrazin-2-ylcarbamoylmethyl)-1-azonia-bicyclo[2.2.2]octane bromide,
(R)-3-(2-Furan-3-yl-2-hydroxy-2-phenyl-acetoxy)-1-(pyrazin-2-ylcarbamoylmethyl)-1-azonia-bicyclo[2.2.2]octane bromide,
(R)-3-(2,2-Di-furan-3-yl-2-hydroxy-acetoxy)-1-(pyrazin-2-ylcarbamoylmethyl)-1-azonia-bicyclo[2.2.2]octane bromide,
(R)-3-(2-Cyclohexyl-2-hydroxy-2-thiophen-3-yl-acetoxy)-1-(pyrazin-2-ylcarbamoylmethyl)-1-azonia-bicyclo[2.2.2]octane bromide,
(R)-3-(2-Cyclopentyl-2-hydroxy-2-thiophen-3-yl-acetoxy)-1-(pyrazin-2-ylcarbamoylmethyl)-1-azonia-bicyclo[2.2.2]octane bromide,
(R)-3-(2-Hydroxy-2-phenyl-2-thiophen-3-yl-acetoxy)-1-(pyrazin-2-ylcarbamoylmethyl)-1-azonia-bicyclo[2.2.2]octane bromide,
(R)-3-(2-Hydroxy-2,2-di-thiophen-3-yl-acetoxy)-1-(pyrazin-2-ylcarbamoylmethyl)-1-azonia-bicyclo[2.2.2]octane bromide,
(R)-3-(2,2-Dicyclopentyl-2-hydroxy-acetoxy)-1-(pyrazin-2-ylcarbamoylmethyl)-1-azonia-bicyclo[2.2.2]octane bromide,
(R)-3-(2,2-Dicyclohexyl-2-hydroxy-acetoxy)-1-(pyrazin-2-ylcarbamoylmethyl)-1-azonia-bicyclo[2.2.2]octane bromide,
(R)-3-(2-Cyclopentyl-2-hydroxy-2-thiophen-2-yl-acetoxy)-1-(pyrazin-2-ylcarbamoylmethyl)-1-azonia-bicyclo[2.2.2]octane bromide,
(R)-3-(2-Cyclohexyl-2-hydroxy-2-thiophen-2-yl-acetoxy)-1-(pyrazin-2-ylcarbamoylmethyl)-1-azonia-bicyclo[2.2.2]octane bromide,
(R)-3-[2-(3,3-Difluoro-cyclopentyl)-2-hydroxy-2-phenyl-acetoxy]-1-(pyrazin-2-ylcarbamoyl-methyl)-1-azonia-bicyclo[2.2.2]octane bromide,
(R)-3-(9-Hydroxy-9H-fluorene-9-carbonyloxy)-1-(pyrazin-2-ylcarbamoylmethyl)-1-azonia-bicyclo[2.2.2]octane bromide,
(R)-3-(9-Hydroxy-9H-fluorene-9-carbonyloxy)-1-(pyrazin-2-ylcarbamoylmethyl)-1-azonia-bicyclo[2.2.2]octane bromide,
(R)-3-(9-Hydroxy-9H-xanthene-9-carbonyloxy)-1-(pyrazin-2-ylcarbamoylmethyl)-1-azonia-bicyclo[2.2.2]octane bromide,
(R)-3-(9-Hydroxy-9,10-dihydro-anthracene-9-carbonyloxy)-1-(pyrazin-2-ylcarbamoylmethyl)-1-azonia-bicyclo[2.2.2]octane bromide,
(R)-3-(5-Hydroxy-5H-dibenzo[a,d]cycloheptene-5-carbonyloxy)-1-(pyrazin-2-ylcarbamoyl-methyl)-1-azonia-bicyclo[2.2.2]octane bromide,
(R)-3-[2-(3,3-Difluoro-cyclopentyl)-2-hydroxy-2-thiophen-2-yl-acetoxy]-1-(pyrazin-2-yl-carbamoylmethyl)-1-azonia-bicyclo[2.2.2]octane bromide,
(R)-3-[2-(3,3-Difluoro-cyclopentyl)-2-hydroxy-2-thiophen-3-yl-acetoxy]-1-(pyrazin-2-yl-carbamoylmethyl)-1-azonia-bicyclo[2.2.2]octane bromide, (R)-3-(9H-Fluorene-9-carbonyloxy)-1-(pyrazin-2-ylcarbamoylmethyl)-1-azonia-bicyclo[2.2.2]-octane bromide, (R)-3-(9,10-Dihydro-anthracene-9-carbonyloxy)-1-(pyrazin-2-ylcarbamoylmethyl)-1-azonia-bicyclo[2.2.2]octane bromide, and (R)-1-(pyrazin-2-ylcarbamoylmethyl)-3-(9H-xanthene-9-carbonyloxy)-1-azonia-bicyclo[2.2.2]octane bromide.

Examples 209 to 231

The following compounds can be made analogously to Example 1 or as detailed previously in the experimental section:

(R)-3-[2-(2-Chloro-phenyl)-2-hydroxy-2-phenyl-acetoxy]-1-[(5-methyl-isoxazol-3-yl-carbamoyl)-methyl]-1-azonia-bicyclo[2.2.2]octane bromide, (R)-3-(2-Cyclopropyl-2-hydroxy-2-thiophen-2-yl-acetoxy)-1-[(5-methyl-isoxazol-3-yl-carbamoyl)-methyl]-1-azonia-bicyclo[2.2.2]octane bromide, (R)-3-(2-Cyclobutyl-2-hydroxy-2-thiophen-2-yl-acetoxy)-1-[(5-methyl-isoxazol-3-yl-carbamoyl)-methyl]-1-azonia-bicyclo[2.2.2]octane bromide, (R)-3-(2-Cyclohexyl-2-hydroxy-2-thiophen-3-yl-acetoxy)-1-[(5-methyl-isoxazol-3-yl-carbamoyl)-methyl]-1-azonia-bicyclo[2.2.2]octane bromide, (R)-3-(2-Cyclopentyl-2-hydroxy-2-thiophen-3-yl-acetoxy)-1-[(5-methyl-isoxazol-3-yl-carbamoyl)-methyl]-1-azonia-bicyclo[2.2.2]octane bromide, (R)-3-(2-Hydroxy-2,2-di-thiophen-3-yl-acetoxy)-1-[(5-methyl-isoxazol-3-ylcarbamoyl)-methyl]-1-azonia-bicyclo[2.2.2]octane bromide, (R)-3-(2-Hydroxy-2-phenyl-2-thiophen-3-yl-acetoxy)-1-[(5-methyl-isoxazol-3-ylcarbamoyl)-methyl]-1-azonia-bicyclo[2.2.2]octane bromide, (R)-3-[2-(3,3-Difluoro-cyclopentyl)-2-hydroxy-2-phenyl-acetoxy]-1-[(5-methyl-isoxazol-3-ylcarbamoyl)-methyl]-1-azonia-bicyclo[2.2.2]octane bromide, (R)-3-[2-(3,3-Difluoro-cyclopentyl)-2-hydroxy-2-thiophen-2-yl-acetoxy]-1-[(5-methyl-isoxazol-3-ylcarbamoyl)-methyl]-1-azonia-bicyclo[2.2.2]octane bromide, (R)-3-[2-(3,3-Difluoro-cyclopentyl)-2-hydroxy-2-thiophen-3-yl-acetoxy]-1-[(5-methyl-isoxazol-3-ylcarbamoyl)-methyl]-1-azonia-bicyclo[2.2.2]octane bromide, (R)-3-(9H-Fluorene-9-carbonyloxy)-1-[(5-methyl-isoxazol-3-ylcarbamoyl)-methyl]-1-azonia-bicyclo[2.2.2]octane bromide, (R)-3-(9,10-Dihydro-anthracene-9-carbonyloxy)-1-[(5-methyl-isoxazol-3-ylcarbamoyl)-methyl]-1-azonia-bicyclo[2.2.2]octane bromide, (R)-1-[(5-methyl-isoxazol-3-ylcarbamoyl)-methyl]-3-(9H-xanthene-9-carbonyloxy)-1-azonia-bicyclo[2.2.2]octane bromide, (R)-3-(2-Cyclopentyl-2-furan-2-yl-2-hydroxy-acetoxy)-1-[(5-methyl-isoxazol-3-ylcarbamoyl)-methyl]-1-azonia-bicyclo[2.2.2]octane bromide, (R)-3-(2-Cyclohexyl-2-furan-3-yl-2-hydroxy-acetoxy)-1-[(5-methyl-isoxazol-3-ylcarbamoyl)-methyl]-1-azonia-bicyclo[2.2.2]octane bromide, (R)-3-(2-Cyclopentyl-2-furan-3-yl-2-hydroxy-acetoxy)-1-[(5-methyl-isoxazol-3-ylcarbamoyl)-methyl]-1-azonia-bicyclo[2.2.2]octane bromide, (R)-3-(2-Furan-3-yl-2-hydroxy-2-phenyl-acetoxy)-1-[(5-methyl-isoxazol-3-ylcarbamoyl)-methyl]-1-azonia-bicyclo[2.2.2]octane bromide, (R)-3-(2,2-Di-furan-3-yl-2-hydroxy-acetoxy)-1-[(5-methyl-isoxazol-3-ylcarbamoyl)-methyl]-1-azonia-bicyclo[2.2.2]octane bromide, (R)-3-(2,2-Dicyclopentyl-2-hydroxy-acetoxy)-1-[(5-methyl-isoxazol-3-ylcarbamoyl)-methyl]-1-azonia-bicyclo[2.2.2]octane bromide, (R)-3-(2,2-Dicyclohexyl-2-hydroxy-acetoxy)-1-[(5-methyl-isoxazol-3-ylcarbamoyl)-methyl]-1-azonia-bicyclo[2.2.2]octane bromide, (R)-3-(9-Hydroxy-9H-xanthene-9-carbonyloxy)-1-[(5-methyl-isoxazol-3-ylcarbamoyl)-methyl]-1-azonia-bicyclo[2.2.2]octane bromide, (R)-3-(9-Hydroxy-9,10-dihydro-anthracene-9-carbonyloxy)-1-[(5-methyl-isoxazol-3-yl-carbamoyl)-methyl]-1-azonia-bicyclo[2.2.2]octane bromide, and (R)-3-(5-Hydroxy-5H-dibenzo[a,d]cycloheptene-5-carbonyloxy)-1-[(5-methyl-isoxazol-3-yl-carbamoyl)-methyl]-1-azonia-bicyclo[2.2.2]octane bromide.

Examples 232 to 254

The following compounds can be made analogously to Example 1 or as detailed previously in the experimental section:

(R)-3-[2-(2-Chloro-phenyl)-2-hydroxy-2-phenyl-acetoxy]-1-[(5-ethyl-isoxazol-3-ylcarbamoyl)-methyl]-1-azonia-bicyclo[2.2.2]octane bromide, (R)-3-(2-Cyclopropyl-2-hydroxy-2-thiophen-2-yl-acetoxy)-1-[(5-ethyl-isoxazol-3-ylcarbamoyl)-methyl]-1-azonia-bicyclo[2.2.2]octane bromide, (R)-3-(2-Cyclobutyl-2-hydroxy-2-thiophen-2-yl-acetoxy)-1-[(5-ethyl-isoxazol-3-ylcarbamoyl)-methyl]-1-azonia-bicyclo[2.2.2]octane bromide, (R)-3-(2-Cyclohexyl-2-hydroxy-2-thiophen-3-yl-acetoxy)-1-[(5-ethyl-isoxazol-3-ylcarbamoyl)-methyl]-1-azonia-bicyclo[2.2.2]octane bromide, (R)-3-(2-Cyclopentyl-2-hydroxy-2-thiophen-3-yl-acetoxy)-1-[(5-ethyl-isoxazol-3-ylcarbamoyl)-methyl]-1-azonia-bicyclo[2.2.2]octane bromide, (R)-3-(2-Hydroxy-2,2-di-thiophen-3-yl-acetoxy)-1-[(5-ethyl-isoxazol-3-ylcarbamoyl)-methyl]-1-azonia-bicyclo[2.2.2]octane bromide, (R)-3-(2-Hydroxy-2-phenyl-2-thiophen-3-yl-acetoxy)-1-[(5-ethyl-isoxazol-3-ylcarbamoyl)-methyl]-1-azonia-bicyclo[2.2.2]octane bromide, (R)-3-[2-(3,3-Difluoro-cyclopentyl)-2-hydroxy-2-phenyl-acetoxy]-1-[(5-ethyl-isoxazol-3-ylcarbamoyl)-methyl]-1-azonia-bicyclo[2.2.2]octane bromide, (R)-3-[2-(3,3-Difluoro-cyclopentyl)-2-hydroxy-2-thiophen-2-yl-acetoxy]-1-[(5-methyl-isoxazol-3-ylcarbamoyl)-methyl]-1-azonia-bicyclo[2.2.2]octane bromide, (R)-3-[2-(3,3-Difluoro-cyclopentyl)-2-hydroxy-2-thiophen-3-yl-acetoxy]-1-[(5-ethyl-isoxazol-3-ylcarbamoyl)-methyl]-1-azonia-bicyclo[2.2.2]octane bromide, (R)-3-(9H-Fluorene-9-carbonyloxy)-1-[(5-ethyl-isoxazol-3-ylcarbamoyl)-methyl]-1-azonia-bicyclo[2.2.2]octane bromide, (R)-3-(9,10-Dihydro-anthracene-9-carbonyloxy)-1-[(5-ethyl-isoxazol-3-ylcarbamoyl)-methyl]-1-azonia-bicyclo[2.2.2]octane bromide, (R)-1-[(5-ethyl-isoxazol-3-ylcarbamoyl)-methyl]-3-(9H-xanthene-9-carbonyloxy)-1-azonia-bicyclo[2.2.2]octane bromide, (R)-3-(2-Cyclopentyl-2-furan-2-yl-2-hydroxy-acetoxy)-1-[(5-ethyl-isoxazol-3-ylcarbamoyl)-1-azonia-bicyclo[2.2.2]octane bromide, (R)-3-(2-Cyclohexyl-2-furan-3-yl-2-hydroxy-acetoxy)-1-[(5-ethyl-isoxazol-3-ylcarbamoyl)-azonia-bicyclo[2.2.2]octane bromide, (R)-3-(2-Cyclopentyl-2-furan-3-yl-2-hydroxy-acetoxy)-1-[(5-ethyl-isoxazol-3-ylcarbamoyl)-methyl]-1-azonia-bicyclo[2.2.2]octane bromide,
(R)-3-(2-Furan-3-yl-2-hydroxy-2-phenyl-acetoxy)-1-[(5-ethyl-isoxazol-3-ylcarbamoyl)-methyl]-1-azonia-bicyclo[2.2.2]octane bromide,
(R)-3-(2,2-Di-furan-3-yl-2-hydroxy-acetoxy)-1-[(5-ethyl-isoxazol-3-ylcarbamoyl)-methyl]-1-azonia-bicyclo[2.2.2]octane bromide,
(R)-3-(2,2-Dicyclopentyl-2-hydroxy-acetoxy)-1-[(5-ethyl-isoxazol-3-ylcarbamoyl)-methyl]-1-azonia-bicyclo[2.2.2]octane bromide,
(R)-3-(2,2-Dicyclohexyl-2-hydroxy-acetoxy)-1-[(5-ethyl-isoxazol-3-ylcarbamoyl)-methyl]-1-azonia-bicyclo[2.2.2]octane bromide,
(R)-3-(9-Hydroxy-9H-xanthene-9-carbonyloxy)-1-[(5-ethyl-isoxazol-3-ylcarbamoyl)-methyl]-1-azonia-bicyclo[2.2.2]octane bromide,
(R)-3-(9-Hydroxy-9,10-dihydro-anthracene-9-carbonyloxy)-1-[(5-ethyl-isoxazol-3-yl-carbamoyl)-methyl]-1-azonia-bicyclo[2.2.2]octane bromide, and
(R)-3-(5-Hydroxy-5H-dibenzo[a,d]cycloheptene-5-carbonyloxy)-1-[(5-ethyl-isoxazol-3-yl-carbamoyl)-methyl]-1-azonia-bicyclo[2.2.2]octane bromide.

The invention claimed is:
1. A compound of formula I

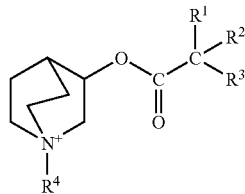

in pharmaceutically acceptable salt form wherein
$R^1$ and $R^2$ are each independently phenyl, one or both of $R^1$ and $R^2$ being substituted at one position by halo, $C_1$-$C_4$-alkyl or $C_1$-$C_4$-alkoxy, and $R^3$ is hydroxy; or
$R^1$ and $R^2$ are each unsubstituted phenyl, and $R^3$ is hydrogen, $C_1$-$C_4$-alkyl or $C_1$-$C_4$-alkoxy; or
$R^1$ is $C_3$-$C_6$-cycloalkyl, and $R^2$ is phenyl, thiophenyl or furanyl, and $R^3$ is hydroxy;
and $R^4$ is $C_1$-$C_4$-alkyl substituted at one, two or three positions by; —CO—NHR$^6$ where R$^6$ is a isoxazolyl optionally substituted by phenyl, or R$^6$ is pyrazinyl or pyrimidinyl.

2. A compound according to claim 1, wherein
$R^1$ and $R^2$ are each independently phenyl, one or both of $R^1$ and $R^2$ being o-halophenyl, o- or p-$C_1$-$C_4$-alkylphenyl or o-, m- or p-$C_1$-$C_4$-alkoxyphenyl, and $R^3$ is hydroxy; or
$R^1$ and $R^2$ are each unsubstituted phenyl, and $R^3$ is hydrogen, $C_1$-$C_4$-alkyl, or $C_1$-$C_4$-alkoxy; or
$R^1$ is $C_5$-$C_6$-cycloalkyl, and $R^2$ is thiophenyl, furanyl or phenyl, and $R^3$ is hydroxy;
and $R^4$ is methyl or 1-ethyl substituted by —CO—NHR$^6$ where R$^6$ is isoxazol-3-yl optionally substituted by phenyl, or R$^6$ is pyrazin-2-yl or pyrimidin-4-yl.

3. A compound according to claim 1 that is selected from
(R)-3-[2,2-Bis-(2-chloro-phenyl)-2-hydroxy-acetoxy]-1-(isoxazol-3-ylcarbamoyl-methyl)-1-azonia-bicyclo[2.2.2]octane.

(R)-3-(2-Hydroxy-2,2-di-p-tolyl-acetoxy)-1-(isoxazol-3-ylcarbamoylmethyl)-1-azonia-bicyclo-[2.2.2]octane,
(R)-3-[2-Hydroxy-2,2-bis-(4-methoxy-phenyl)-acetoxy]-1-(isoxazol-3-ylcarbamoylmethyl)-1-azonia-bicyclo[2.2.2]octane,
(R)-3-(2,2-Diphenyl-propionyloxy)-1-(isoxazol-3-ylcarbamoylmethyl)-1-azonia-bicyclo[2.2.2]-octane,
(R)-3-Diphenylacetoxy-1-(isoxazol-3-ylcarbamoylmethyl)-1-azonia-icyclo[2.2.2]octane,
(R)-1-(Isoxazol-3-ylcarbamoylmethyl)-3-(2-methoxy-2,2-diphenyl-acetoxy)-1-azonia-bicyclo-[2.2.2]octane,
(R)-3-(2-Cyclohexyl-2-hydroxy-2-phenyl-acetoxy)-1-(isoxazol-3-ylcarbamoylmethyl)-1-azonia-bicyclo[2.2.2]octane,
(R)-3-(2-Cyclopentyl-2-hydroxy-2-thiophen-2-yl-acetoxy)-1-(isoxazol-3-ylcarbamoylmethyl)-1-azonia-bicyclo[2.2.2]octane,
(R)-3-(2-Cyclohexyl-2-hydroxy-2-thiophen-2-yl-acetoxy)-1-(isoxazol-3-ylcarbamoylmethyl)-1-azonia-bicyclo[2.2.2]octane,
(R)-3-(2-Cyclopentyl-2-hydroxy-2-phenyl-acetoxy)-1-(isoxazol-3-ylcarbamoyl-methyl)-1-azonia-bicyclo[2.2.2]octane,
(R)-3-(2-Cyclopentyl-2-hydroxy-2-phenyl-acetoxy)-1-(pyrazin-2-ylcarbamoylmethyl)-1-azonia-bicyclo[2.2.2]octane,
(R)-3-(2-Cyclohexyl-2-hydroxy-2-phenyl-acetoxy)-1-(pyrimidin-4-ylcarbamoylmethyl)-1-azonia-bicyclo[2.2.2]octane,
(R)-3-(2-Cyclohexyl-2-hydroxy-2-phenyl-acetoxy)-1-[(4-phenyl-isoxazol-3-ylcarbamoyl)-methyl]-1-azonia-bicyclo[2.2.2]octane,
(R)-3-[2-Hydroxy-2,2-bis-(3-methoxy-phenyl)-acetoxy]-1-(isoxazol-3-ylcarbamoylmethyl)-1-azonia-bicyclo[2.2.2]octane,
(R)-3-(2-Cyclopentyl-2-hydroxy-2-thiophen-2-yl-acetoxy)-1-pyrazin-2-ylcarbamoylmethyl)-1-azonia-bicyclo[2.2.2]octane,
(R)-3-(2-Cyclohexyl-2-hydroxy-2-phenyl-acetoxy)-1-(pyrazin-2-ylcarbamoylmethyl)-1-azonia-bicyclo[2.2.2]octane,
(R)-3-[2-Hydroxy-2-(4-methoxy-phenyl)-2-phenyl-acetoxy]-1-(isoxazol-3-ylcarbamoylmethyl)-1-azonia-bicyclo[2.2.2]octane,
(R)-3-(2-Hydroxy-2-phenyl-2-o-tolyl-acetoxy)-1-(isoxazol-3-ylcarbamoylmethyl)-1-azonia-bicyclo[2.2.2]octane,
(R)-3-[2-Hydroxy-2-(2-methoxy-phenyl)-2-phenyl-acetoxy]-1-(isoxazol-3-ylcarbamoylmethyl)-1-azonia-bicyclo[2.2.2]octane,
(R)-3-(2-Cyclopentyl-2-hydroxy-2-phenyl-acetoxy)-1-(pyrimidin-4-ylcarbamoylmethyl)-1-azonia-bicyclo[2.2.2]octane,
(R)-3-(2-Cyclopentyl-2-hydroxy-2-thiophen-2-yl-acetoxy)-1-(pyrimidin-4-yl carbamoylmethyl)-1-azonia-bicyclo[2.2.2]octane,
(R)-3-(2-Cyclohexyl-2-hydroxy-2-thiophen-2-yl-acetoxy)-1-(pyrimidin-4-yl-carbamoylmethyl)-1-azonia-bicyclo[2.2.2]octane, and
(R)-3-(2-Cyclopentyl-2-furan-2-yl-2-hydroxy-acetoxy)-1-(isoxazol-3-ylcarbamoylmethyl)-1-azonia-bicyclo[2.2.2]octane.

4. A compound according to claim 1 that is selected from
(R)-3-[2,2-Bis-(2-chloro-phenyl)-2-hydroxy-acetoxy]-1-(isoxazol-3-ylcarbamoyl-methyl)-1-azonia-bicyclo[2.2.2]octane bromide, (R)-3-(2-Hydroxy-2,2-di-p-tolyl-acetoxy)-1-(isoxazol-3-ylcarbamoylmethyl)-1-azonia-bicyclo-[2.2.2]octane bromide,
(R)-3-[2-Hydroxy-2,2-bis-(4-methoxy-phenyl)-acetoxy]-1-(isoxazol-3-ylcarbamoyl methyl)-1-azonia-bicyclo [2.2.2]octane bromide,
(R)-3-(2,2-Diphenyl-propionyloxy)-1-(isoxazol-3-ylcarbamoylmethyl)-1-azonia-bicyclo[2.2.2]-octane bromide,
(R)-3-Diphenylacetoxy-1-(isoxazol-3-ylcarbamoylmethyl)-1-azonia-icyclo[2.2.2]octane bromide,
(R)-1-(Isoxazol-3-ylcarbamoylmethyl)-3-(2-methoxy-2,2-diphenyl-acetoxy)-1-azonia-bicyclo-[2.2.2]octane bromide,
(R)-3-(2-Cyclohexyl-2-hydroxy-2-phenyl-acetoxy)-1-(isoxazol-3-ylcarbamoylmethyl)-1-azonia-bicyclo [2.2.2]octane bromide,
(R)-3-(2-Cyclopentyl-2-hydroxy-2-thiophen-2-yl-acetoxy)-1-(isoxazol-3-ylcarbamoylmethyl)-1-azonia-bicyclo[2.2.2]octane bromide,
(R)-3-(2-Cyclohexyl-2-hydroxy-2-thiophen-2-yl-acetoxy)-1-(isoxazol-3-ylcarbamoylmethyl)-1-azonia-bicyclo[2.2.2]octane bromide,
(R)-3-(2-Cyclopentyl-2-hydroxy-2-phenyl-acetoxy)-1-(isoxazol-3-ylcarbamoyl-methyl)-1-azonia-bicyclo [2.2.2]octane bromide,
(R)-3-(2-Cyclopentyl-2-hydroxy-2-phenyl-acetoxy)-1-(pyrazin-2-ylcarbamoylmethyl)-1-azonia-bicyclo [2.2.2]octane bromide,
(R)-3-(2-Cyclohexyl-2-hydroxy-2-phenyl-acetoxy)-1-(pyrimidin-4-ylcarbamoylmethyl)-1-azonia-bicyclo [2.2.2]octane bromide,
(R)-3-(2-Cyclohexyl-2-hydroxy-2-phenyl-acetoxy)-1-[(4-phenyl-isoxazol-3-ylcarbamoyl)-methyl]-1-azonia-bicyclo[2.2.2]octane bromide,
(R)-3-[2-Hydroxy-2,2-bis-(3-methoxy-phenyl)-acetoxy]-1-(isoxazol-3-ylcarbamoylmethyl)-1-azonia-bicyclo[2.2.2]octane bromide,
(R)-3-(2-Cyclopentyl-2-hydroxy-2-thiophen-2-yl-acetoxy)-1-pyrazin-2-ylcarbamoylmethyl)-1-azonia-bicyclo[2.2.2]octane bromide,
(R)-3-(2-Cyclohexyl-2-hydroxy-2-phenyl-acetoxy)-1-(pyrazin-2-ylcarbamoylmethyl)-azonia-bicyclo[2.2.2] octane bromide,
(R)-3-[2-Hydroxy-2-(4-methoxy-phenyl)-2-phenyl-acetoxy]-1-(isoxazol-3-ylcarbamoylmethyl)-1-azonia-bicyclo[2.2.2]octane bromide,
(R)-3-(2-Hydroxy-2-phenyl-2-o-tolyl-acetoxy)-1-(isoxazol-3-ylcarbamoylmethyl)-1-azonia-bicyclo[2.2.2]octane bromide,
(R)-3-[2-Hydroxy-2-(2-methoxy-phenyl)-2-phenyl-acetoxy]-1-(isoxazol-3-ylcarbamoylmethyl)-1-azonia-bicyclo[2.2.2]octane bromide,
(R)-3-(2-Cyclopentyl-2-hydroxy-2-phenyl-acetoxy)-1-(pyrimidin-4-ylcarbamoylmethyl)-1-azonia-bicyclo [2.2.2]octane bromide,
(R)-3-(2-Cyclopentyl-2-hydroxy-2-thiophen-2-yl-acetoxy)-1-(pyrimidin-4-yl carbamoylmethyl)-1-azonia-bicyclo[2.2.2]octane bromide,
(R)-3-(2-Cyclohexyl-2-hydroxy-2-thiophen-2-yl-acetoxy)-1-(pyrimidin-4-yl-carbamoylmethyl)-1-azonia-bicyclo[2.2.2]octane bromide, and
(R)-3-(2-Cyclopentyl-2-furan-2-yl-2-hydroxy-acetoxy)-1-(isoxazol-3-ylcarbamoylmethyl)-1-azonia-bicyclo [2.2.2]octane bromide.

5. A compound according to claim 1 that is selected from
(R)-3-((S)-2-Cyclohexyl-2-hydroxy-2-thiophen-2-yl-acetoxy)-1-(isoxazol-3-ylcarbamoylmethyl)-1-azonia-bicyclo[2.2.2]octane phosphate,
(R)-3-((R)-2-Cyclohexyl-2-hydroxy-2-phenyl-acetoxy)-1-(isoxazol-3-ylcarbamoylmethyl)-1-azonia-bicyclo [2.2.2]octane phosphate, and
(R)-3-((R)-2-Cyclopentyl-2-hydroxy-2-phenyl-acetoxy)-1-(isoxazol-3-yl-carbamoylmethyl)-1-azonia-bicyclo [2.2.2]octane phosphate.

6. A pharmaceutical composition comprising as active ingredient a compound according to claim 1, optionally together with a pharmaceutically acceptable diluent or carrier.

7. A process for the preparation of a compound of formula I according to claim 1, which comprises
(i) (A) reacting a compound of formula II

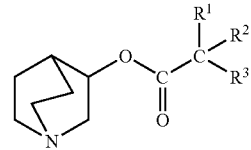

where $R^1$, $R^2$ and $R^3$ are as defined in claim 1, with a compound of formula III

where $R^4$ is as defined in claim 1 and X is chloro, bromo or iodo; or
(B) reacting a compound of formula IV

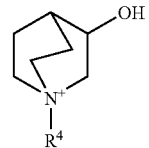

or a sodium salt thereof, where $R^4$ is as defined in claim 1, with a compound of formula V

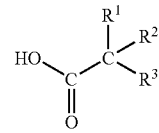

where $R^1$, $R^2$ and $R^3$ are as defined in claim 1; and
(ii) recovering the compound of formula I.

* * * * *